(12) United States Patent
Ravuna et al.

(10) Patent No.: US 12,239,449 B2
(45) Date of Patent: Mar. 4, 2025

(54) SYSTEM AND METHOD TO DETECT STABLE ARRHYTHMIA HEARTBEAT AND TO CALCULATE AND DETECT CARDIAC MAPPING ANNOTATIONS

(71) Applicant: Biosense Webster (Israel) Ltd., Yokneam (IL)

(72) Inventors: Eliyahu Ravuna, Kiryat Ata (IL); Lior Botzer, Timrat (IL); Jonathan Yarnitsky, Haifa (IL); Elad Nakar, Timrat (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 521 days.

(21) Appl. No.: 17/341,917

(22) Filed: Jun. 8, 2021

(65) Prior Publication Data
US 2021/0386355 A1   Dec. 16, 2021

Related U.S. Application Data

(60) Provisional application No. 63/037,259, filed on Jun. 10, 2020.

(51) Int. Cl.
*A61B 5/00*   (2006.01)
*A61B 5/0205*   (2006.01)
(Continued)

(52) U.S. Cl.
CPC ............ *A61B 5/367* (2021.01); *A61B 5/0205* (2013.01); *A61B 5/0816* (2013.01); *A61B 5/282* (2021.01); *A61B 5/283* (2021.01); *A61B 5/339* (2021.01); *A61B 5/6844* (2013.01); *A61B 5/7221* (2013.01); *A61B 5/7267* (2013.01);
(Continued)

(58) Field of Classification Search
None
See application file for complete search history.

(56) References Cited

U.S. PATENT DOCUMENTS

| | | | |
|---|---|---|---|
| 5,715,829 A | 2/1998 | Arand et al. | |
| 2009/0099468 A1* | 4/2009 | Thiagalingam | A61B 5/349 600/515 |

(Continued)

OTHER PUBLICATIONS

European Search Report for corresponding EPA No. 21178840.1 dated Oct. 13, 2021.
(Continued)

*Primary Examiner* — Sana Sahand
(74) *Attorney, Agent, or Firm* — Volpe Koenig

(57) ABSTRACT

A system and method for detecting a mapping annotation for an electrophysiological (EP) mapping system. The system includes a processor comprising a machine learning algorithm configured to receive a first heartbeat at an identified cardiac spatial location including a first set of attributes information corresponding to the first heartbeat; receive a second heartbeat at the identified cardiac spatial location including a second set of attributes information corresponding to the second heartbeat; compare the first set of attributes information with the second set of attributes information;
(Continued)

and determine which of the first heartbeat and the second heartbeat has optimal characteristics based on the compared attribute information.

22 Claims, 24 Drawing Sheets

(51) Int. Cl.
| | | |
|---|---|---|
| *A61B 5/08* | (2006.01) | |
| *A61B 5/282* | (2021.01) | |
| *A61B 5/283* | (2021.01) | |
| *A61B 5/339* | (2021.01) | |
| *A61B 5/367* | (2021.01) | |
| *G06N 3/044* | (2023.01) | |
| *G06N 3/08* | (2023.01) | |
| *G16H 40/63* | (2018.01) | |
| *G16H 50/20* | (2018.01) | |
| *G16H 50/30* | (2018.01) | |
| *G16H 50/70* | (2018.01) | |
| *G16H 70/60* | (2018.01) | |

(52) U.S. Cl.
CPC .............. *G06N 3/044* (2023.01); *G06N 3/08* (2013.01); *G16H 40/63* (2018.01); *G16H 50/20* (2018.01); *G16H 50/30* (2018.01); *G16H 50/70* (2018.01); *G16H 70/60* (2018.01)

(56) References Cited

U.S. PATENT DOCUMENTS

| | | | |
|---|---|---|---|
| 2012/0184865 A1* | 7/2012 | Harlev | A61B 5/283 |
| | | | 600/509 |
| 2013/0123652 A1 | 5/2013 | Rubinstein | |
| 2016/0352727 A1 | 12/2016 | Day | |
| 2018/0042504 A1 | 2/2018 | Botzer et al. | |
| 2018/0160983 A1* | 6/2018 | Galloway | A61B 5/332 |
| 2018/0296167 A1* | 10/2018 | Stewart | G06T 17/00 |
| 2018/0350468 A1 | 12/2018 | Friedman | |
| 2019/0030331 A1 | 1/2019 | Ghosh | |

OTHER PUBLICATIONS

Li Qiao et al., "A machine learning approach to multi-level ECG signal quality classification", Computer Methods and Programs in Biomedicine, vol. 117, No. 3, Sep. 18, 2014, pp. 435-447.

Zhang Qifei et al., "A Cascaded Assessing Signal Quality of Dynamic ECG", vol. 2019, Oct. 20, 2019, pp. 1-12.

Communication pursuant to Article 94(3) EPC for European Patent Application No. 21 178 840.1 dated Jun. 28, 2024.

* cited by examiner

610

| Weather | Play |
|---|---|
| Sunny | No |
| Overcast | Yes |
| Rainy | Yes |
| Sunny | Yes |
| Sunny | Yes |
| Overcast | Yes |
| Rainy | No |
| Rainy | No |
| Sunny | Yes |
| Rainy | Yes |
| Sunny | No |
| Overcast | Yes |
| Overcast | Yes |
| Rainy | No |

620

Frequency Table

| Weather | No | Yes |
|---|---|---|
| Overcast | | 4 |
| Rainy | 3 | 2 |
| Sunny | 2 | 3 |
| Grand Total | 5 | 9 |

630

Likelihood Table

| Weather | No | Yes | | |
|---|---|---|---|---|
| Overcast | | 4 | =4/14 | 0.20 |
| Rainy | 3 | 2 | =5/14 | 0.36 |
| Sunny | 2 | 3 | =5/14 | 0.36 |
| All | 5 | 9/14 | | |
| | =5/14 | 0.64 | | |
| | 0.36 | | | |

FIG. 6

SYSTEM AND METHOD TO DETECT STABLE ARRHYTHMIA HEARTBEAT AND TO CALCULATE AND DETECT CARDIAC MAPPING ANNOTATIONS

CROSS REFERENCE TO RELATED APPLICATION

This application claims the benefit of U.S. Provisional Application No. 63/037,259, filed Jun. 10, 2020, the contents of which are incorporated by reference as if fully set forth.

FIELD OF INVENTION

The present disclosure is related to artificial intelligence and machine learning associated with selecting an optimal heartbeat at each spatial location in stable cardiac arrhythmias and calculating and detecting optimal cardiac mapping annotations.

BACKGROUND

Treatments for cardiac conditions such as cardiac arrhythmia often require obtaining a detailed mapping of cardiac tissue, chambers, veins, arteries and/or electrical pathways. For example, as a prerequisite to performing a catheter ablation, the cause of the cardiac arrhythmia must be accurately located in the heart chamber. Such locating may be done via an electrophysiological investigation during which electrical potentials are detected spatially resolved with a mapping catheter introduced into the heart chamber. This electrophysiological investigation, often referred to as electrophysiological (EP) cardiac mapping or cardiac electroanatomical (EA) mapping, provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time.

Mapping of cardiac areas such as cardiac regions, tissue, veins, arteries and/or electrical pathways of the heart may result in identifying problem areas such as scar tissue, arrhythmia sources (e.g., electric rotors), healthy areas, and the like. Cardiac areas may be mapped such that a visual rendering of the mapped cardiac areas is provided using a display, as further disclosed herein. Additionally, cardiac mapping may include mapping based on one or more modalities such as, but not limited to local activation time (LAT), an electrical activity, a topology, a bipolar mapping, a dominant frequency, or an impedance. Data corresponding to multiple modalities may be captured using a catheter inserted into a patient's body and may be provided for rendering at the same time or at different times based on corresponding settings and/or preferences of a medical professional.

Electrocardiograms (ECGs) and electrograms (EGMs) are examples of heart mapping. ECGs are generated from electrical signals from a heart that describe heart activity. ECGs are utilized during cardiac procedures to identify potential origination locations of cardiac conditions. ECGs signals may also be used to map portions of a heart. EGMs may be recorded from each of the electrodes in contact with a cardiac surface relative to a temporal reference such as the onset of a P-wave in sinus rhythm from a body surface ECG. ECG and EGM signals can be utilized with rules-based algorithms to determine cardiac mapping annotations, such as that described in U.S. Patent Publication No. US2018/0042504. However, during cardiac procedures, physicians may need to manually fix incorrect mapping annotations.

EP cardiac mapping systems conventionally acquire and record a first heartbeat at every spatial location, even if the heartbeat has poor characteristics. A need exists for an improved method and system to select and detect the best heartbeat at each spatial location as a mapping annotation. In addition, a need exists for an improved method and system to determine cardiac mapping annotations.

SUMMARY

Methods, apparatuses, systems, and models for selecting an optimal heartbeat at each spatial location in stable cardiac arrhythmias and calculating and detecting optimal cardiac mapping annotations are described herein.

In accordance with one aspect, the subject matter disclosed herein relates to a system for detecting a heartbeat with optimal characteristics for an electrophysiological (EP) mapping system. The system includes a processor comprising a machine learning algorithm configured to receive a first heartbeat at an identified cardiac spatial location including a first set of attributes information corresponding to the first heartbeat; receive a second heartbeat at the identified cardiac spatial location including a second set of attributes information corresponding to the second heartbeat; compare the first set of attributes information with the second set of attributes information; and determine which of the first heartbeat and the second heartbeat has optimal characteristics based on the compared attribute information.

In accordance with another aspect, the subject matter disclosed herein relates to a method for detecting a heartbeat with optimal characteristics for an EP mapping system by a machine learning algorithm. The method includes receiving first data comprising a first heartbeat at an identified cardiac spatial location including first attribute information corresponding to the first heartbeat; receiving second data comprising a second heartbeat at the identified cardiac spatial location including second attribute information corresponding to the second heartbeat; comparing the first data with the second data; and outputting a binary determination of which of the first heartbeat and the second heartbeat has optimal characteristics based on the comparing.

In accordance with yet another aspect, the subject matter disclosed herein relates to a system for detecting a mapping annotation for an EP mapping system. The system includes a processor comprising a machine learning algorithm configured to: receive input data comprising attribute data for each of a plurality of heartbeats obtained at the same spatial location; compare the attribute data for each of a plurality of heartbeats with predefined threshold values; and determine which heartbeat to use as the mapping annotation based on the heartbeat with best attribute data.

In accordance with yet another aspect, the subject matter disclosed herein relates to a method for detecting a mapping annotation for an EP mapping system by a machine learning algorithm. The method includes receiving input data comprising attribute data for each of a plurality of heartbeats obtained at the same spatial location; comparing the attribute data for each of a plurality of heartbeats with predefined threshold values; determining which heartbeat to use as the mapping annotation based on the heartbeat with best attribute data; and outputting the determination to the EP mapping system.

In accordance with yet another aspect, the subject matter disclosed herein relates to a system for determining a mapping annotation for an EP mapping system. The system includes a processor comprising a machine learning algorithm configured to receive first EP signal data obtained from a cardiac location; determine an initial mapping annotation based on the first EP signal data; receive data relating to a manually corrected mapping annotation; receive second EP signal data obtained from the cardiac location; and determine a new mapping annotation based on the second EP signal data and the manually corrected mapping annotation.

In accordance with yet another aspect, the subject matter disclosed herein relates to a method for determining a mapping annotation for an EP mapping system by a machine learning algorithm. The method includes receiving first EP signal data obtained from a cardiac location; determining an initial mapping annotation based on the first EP signal data; receiving data relating to a manually corrected mapping annotation at the cardiac location; receiving second EP signal data obtained from the cardiac location; and determining a new mapping annotation based on the second EP signal data and the manually corrected mapping annotation.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 6 illustrates an example of the probabilities of a naive Bayes calculation in accordance with the subject matter of the present application;

DETAILED DESCRIPTION

Systems and methods are provided for selecting and detecting the best heartbeat at each spatial location as a mapping annotation and for improving the determination of cardiac mapping annotations based on machine learning.

Figure 1:
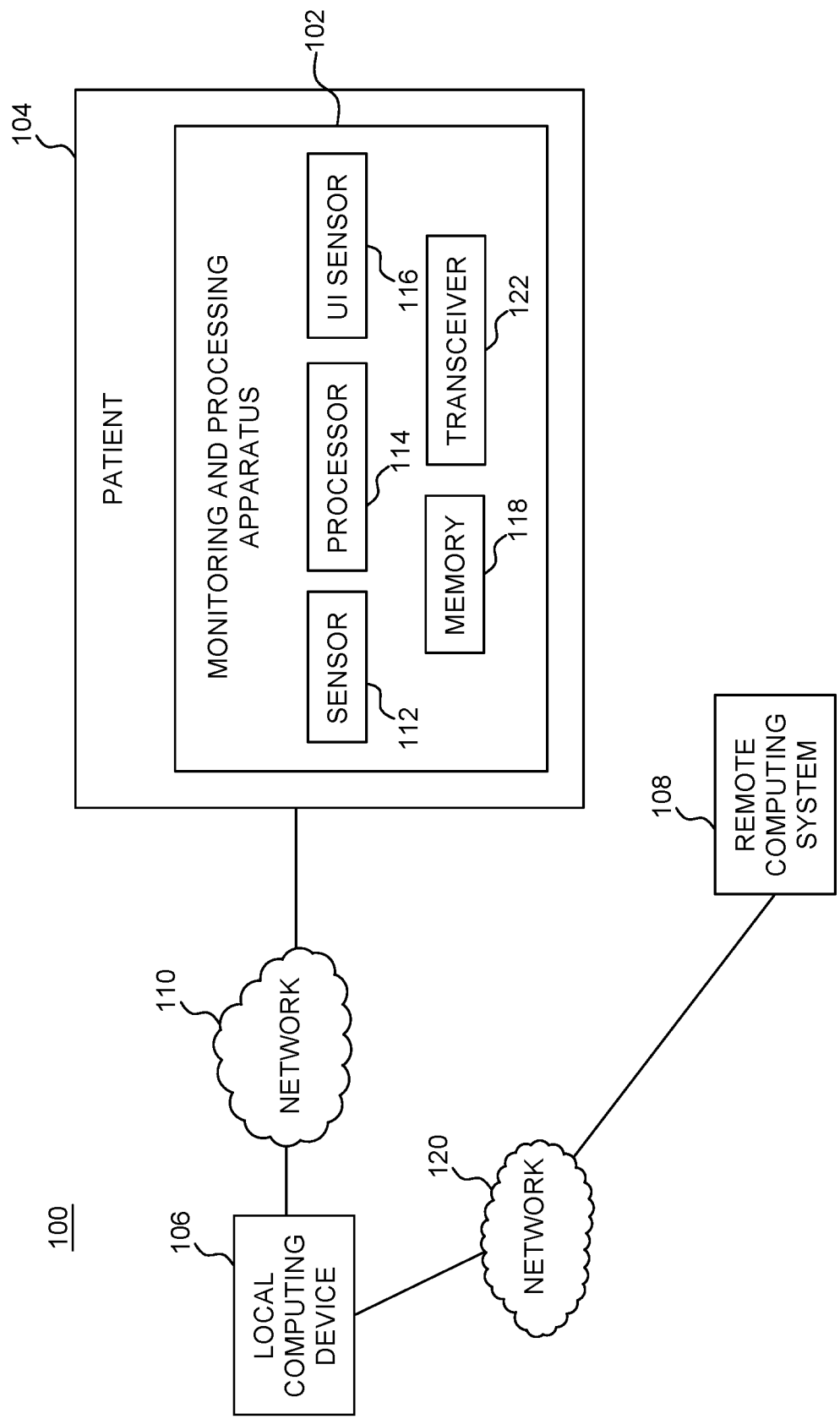
FIG. 1 is a block diagram of an example system for remotely monitoring and communicating patient biometrics in accordance with the subject matter of the present application.

FIG. 1 is a block diagram of an example system 100 for remotely monitoring and communicating patient biometrics (i.e., patient data). In the example illustrated in FIG. 1, the system 100 includes a patient biometric monitoring and processing apparatus 102 associated with a patient 104, a local computing device 106, a remote computing system 108, a first network 110 and a second network 120.

According to an exemplary embodiment, a monitoring and processing apparatus 102 may be an apparatus that is internal to the patient's body (e.g., subcutaneously implantable). The monitoring and processing apparatus 102 may be inserted into a patient via any applicable manner including orally injecting, surgical insertion via a vein or artery, an endoscopic procedure, or a laparoscopic procedure.

According to an exemplary embodiment, a monitoring and processing apparatus 102 may be an apparatus that is external to the patient. For example, as described in more detail below, the monitoring and processing apparatus 102 may include an attachable patch (e.g., that attaches to a patient's skin). The monitoring and processing apparatus 102 may also include a catheter with one or more electrodes, a probe, a blood pressure cuff, a weight scale, a bracelet or smart watch biometric tracker, a glucose monitor, a continuous positive airway pressure (CPAP) machine or virtually any device which may provide an input concerning the health or biometrics of the patient.

According to an exemplary embodiment, a monitoring and processing apparatus 102 may include both components that are internal to the patient and components that are external to the patient.

A single monitoring and processing apparatus 102 is shown in FIG. 1. Example systems may, however, may include a plurality of patient biometric monitoring and processing apparatuses. A patient biometric monitoring and processing apparatus may be in communication with one or more other patient biometric monitoring and processing apparatuses. Additionally, or alternatively, a patient biometric monitoring and processing apparatus may be in communication with the first network 110.

One or more monitoring and processing apparatuses 102 may acquire patient biometric data (e.g., electrical signals, blood pressure, temperature, blood glucose level or other biometric data) and receive at least a portion of the patient biometric data representing the acquired patient biometrics and additional formation associated with acquired patient biometrics from one or more other monitoring and processing apparatuses 102. The additional information may be, for example, diagnosis information and/or additional information obtained from an additional device such as a wearable device. Each monitoring and processing apparatus 102 may process data, including its own acquired patient biometrics as well as data received from one or more other monitoring and processing apparatuses 102.

In FIG. 1, the first network 110 is an example of a short-range network (e.g., local area network (LAN), or personal area network (PAN)). Information may be sent, via short-range network 110, between monitoring a processing apparatus 102 and local computing device 106 using any one of various short-range wireless communication protocols, such as Bluetooth, Wi-Fi, Zigbee, Z-Wave, near field communications (NFC), ultraband, Zigbee, or infrared (IR).

In an exemplary embodiment, the second network 120 may be a wired network, a wireless network or include one or more wired and wireless networks. For example, the second network 120 may be a long-range network (e.g., wide area network (WAN), the internet, or a cellular network). Information may be sent, via the second network 120 using any one of various long-range wireless communication protocols (e.g., TCP/IP, HTTP, 3G, 4G/LTE, or 5G/New Radio).

In an exemplary embodiment, the patient monitoring and processing apparatus 102 may include a patient biometric sensor 112, a processor 114, a user input (UI) sensor 116, a memory 118, and a transmitter-receiver (i.e., transceiver) 122. The patient monitoring and processing apparatus 102 may continually or periodically monitor, store, process and communicate, via the first network 110, any number of various patient biometrics. Examples of patient biometrics include electrical signals (e.g., electrocardiogram (ECG) signals and brain biometrics), blood pressure data, blood glucose data and temperature data. The patient biometrics may be monitored and communicated for treatment across any number of various diseases, such as cardiovascular diseases (e.g., arrhythmias, cardiomyopathy, and coronary artery disease) and autoimmune diseases (e.g., type I and type II diabetes).

In an embodiment, patient biometric sensor 112 may include, for example, one or more sensors configured to sense a type of biometric patient biometrics. For example, patient biometric sensor 112 may include an electrode configured to acquire electrical signals (e.g., heart signals, brain signals or other bioelectrical signals), a temperature sensor, a blood pressure sensor, a blood glucose sensor, a blood oxygen sensor, a pH sensor, an accelerometer and a microphone.

In an exemplary embodiment, as described in more detail below, patient biometric monitoring and processing apparatus 102 may be an ECG monitor for monitoring ECG signals of a heart. The patient biometric sensor 112 of the ECG monitor may include one or more electrodes for acquiring ECG signals. The ECG signals may be used for treatment of various cardiovascular diseases.

In an exemplary embodiment, transceiver 122 may include a separate transmitter and receiver. Alternatively, transceiver 122 may include a transmitter and receiver integrated into a single device.

In an exemplary embodiment, processor 114 may be configured to store patient data, such as patient biometric data in memory 118 acquired by patient biometric sensor 112, and communicate the patient data, across the first network 110, via a transmitter of transceiver 122. Data from one or more other monitoring and processing apparatus 102 may also be received by a receiver of transceiver 122, as described in more detail below.

According to an exemplary embodiment, the monitoring and processing apparatus 102 includes UI sensor 116 which may be, for example, a piezoelectric sensor or a capacitive sensor configured to receive a user input, such as a tapping or touching. For example, UI sensor 116 may be controlled to implement a capacitive coupling, in response to tapping or touching a surface of the monitoring and processing apparatus 102 by the patient 104. Gesture recognition may be implemented via any one of various capacitive types, such as resistive capacitive, surface capacitive, projected capacitive, surface acoustic wave, piezoelectric and infrared touching. Capacitive sensors may be disposed at a small area or over a length of the surface such that the tapping or touching of the surface activates the monitoring device.

As described in more detail below, the processor 114 may be configured to respond selectively to different tapping patterns of the capacitive sensor (e.g., a single tap or a double tap), which may be the UI sensor 116, such that different tasks of the patch (e.g., acquisition, storing, or transmission of data) may be activated based on the detected pattern. In some embodiments, audible feedback may be given to the user from processing apparatus 102 when a gesture is detected.

In an exemplary embodiment, the local computing device 106 of system 100 is in communication with the patient biometric monitoring and processing apparatus 102 and may be configured to act as a gateway to the remote computing system 108 through the second network 120. The local computing device 106 may be, for example, a, smart phone, smartwatch, tablet or other portable smart device configured to communicate with other devices via the second network 120. Alternatively, the local computing device 106 may be a stationary or standalone device, such as a stationary base station including, for example, modem and/or router capability, a desktop or laptop computer using an executable program to communicate information between the processing apparatus 102 and the remote computing system 108 via the PC's radio module, or a Universal Serial Bus (USB) dongle. Patient biometrics may be communicated between the local computing device 106 and the patient biometric monitoring and processing apparatus 102 using a short-range wireless technology standard (e.g., Bluetooth, Wi-Fi, ZigBee, Z-wave and other short-range wireless standards) via the short-range wireless network 110, such as a LAN (e.g., a PAN). In some embodiments, the local computing device 106 may also be configured to display the acquired patient electrical signals and information associated with the acquired patient electrical signals, as described in more detail below.

In some exemplary embodiments, remote computing system 108 may be configured to receive at least one of the monitored patient biometrics and information associated with the monitored patient via the second network 120, which is a long-range network. For example, if the local computing device 106 is a mobile phone, the second network 120 may be a wireless cellular network, and information may be communicated between the local computing device 106 and the remote computing system 108 via a wireless technology standard, such as any of the wireless technologies mentioned above. As described in more detail below, the remote computing system 108 may be configured to provide (e.g., visually display and/or aurally provide) the at least one of the patient biometrics and the associated information to a healthcare professional (e.g., a physician).

Figure 2:
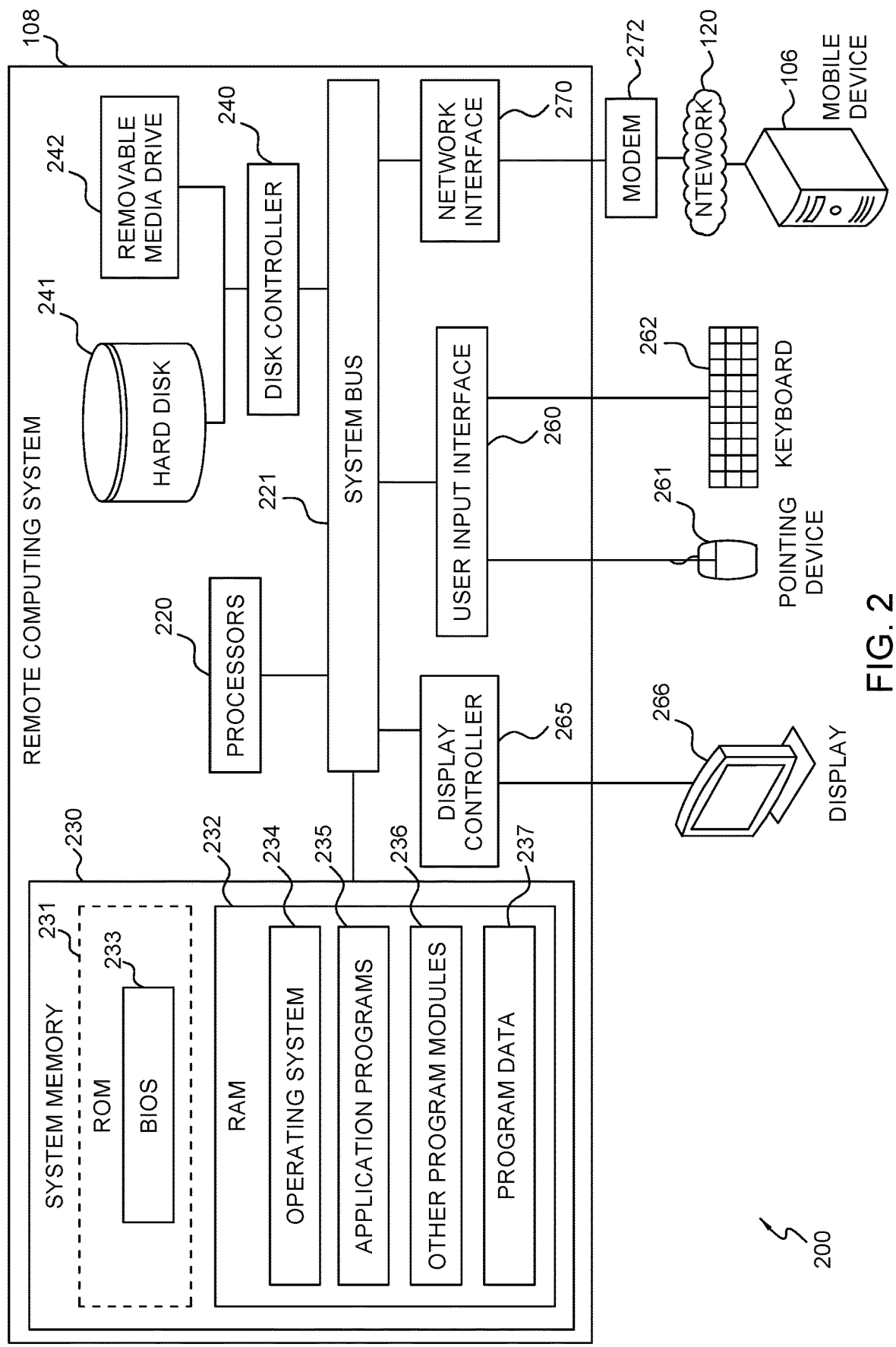
FIG. 2 is a system diagram of an exemplary computing environment in communication with network in accordance with the subject matter of the present application.

FIG. 2 is a system diagram of an example of a computing environment 200 in communication with the second network 120. In some instances, the computing environment 200 is incorporated in a public cloud computing platform (such as Amazon Web Services or Microsoft Azure), a hybrid cloud computing platform (such as HP Enterprise OneSphere) or a private cloud computing platform.

As shown in FIG. 2, computing environment 200 preferably includes remote computing system 108, which is one example of a computing system upon which embodiments described herein may be implemented.

The remote computing system 108 may, via processors 220, which may include one or more processors, perform various functions. For example, the functions may include analyzing monitored patient biometrics and the associated information and, according to physician-determined or algorithm driven thresholds and parameters, providing (e.g., via display 266) alerts, additional information or instructions. As described in more detail below, the remote computing system 108 may be used to provide (e.g., via display 266) healthcare personnel (e.g., a physician) with a dashboard of patient information, such that such information may enable healthcare personnel to identify and prioritize patients having more critical needs than others.

As shown in FIG. 2, the remote computing system 108 may include a communication mechanism such as a bus 221 or other communication mechanism for communicating information within the remote computing system 108. The remote computing system 108 further includes one or more processors 220 coupled with the bus 221 for processing the information. The processors 220 may include one or more central processing units (CPUs), graphics processing units (GPUs), or any other processor known in the art.

The remote computing system 108 also may include a system memory 230 coupled to the bus 221 for storing information and instructions to be executed by processors 220. The system memory 230 may include computer readable storage media in the form of volatile and/or nonvolatile memory, such as read only system memory (ROM) 231 and/or random-access memory (RAM) 232. The system memory RAM 232 may include other dynamic storage device(s) (e.g., dynamic RAM, static RAM, and synchronous DRAM). The system memory ROM 231 may include other static storage device(s) (e.g., programmable ROM, erasable PROM, and electrically erasable PROM). In addition, the system memory 230 may be used for storing temporary variables or other intermediate information during the execution of instructions by the processors 220. A basic input/output system 233 (BIOS) may contain routines to transfer information between elements within remote computing system 108, such as during start-up, that may be stored in system memory ROM 231. RAM 232 may comprise data and/or program modules that are immediately accessible to and/or presently being operated on by the processors 220. System memory 230 may additionally include, for example, operating system 234, application programs 235, other program modules 236 and program data 237.

In an exemplary embodiment, the remote computing system 108 may also include a disk controller 240 coupled to the bus 221 to control one or more storage devices for storing information and instructions, such as a magnetic hard disk 241 and a removable media drive 242 (e.g., floppy disk drive, compact disc drive, tape drive, and/or solid state drive). The storage devices may be added to the remote computing system 108 using an appropriate device interface (e.g., a small computer system interface (SCSI), integrated device electronics (IDE), USB, or FireWire).

The remote computing system 108 may also include a display controller 265 coupled to the bus 221 to control a monitor or display 266, such as a cathode ray tube (CRT) or liquid crystal display (LCD), for displaying information to a computer user. The illustrated remote computing system 108 includes a user input interface 260 and one or more input devices, such as a keyboard 262 and a pointing device 261, for interacting with a computer user and providing information to the processors 220. The pointing device 261, for example, may be a mouse, a trackball, or a pointing stick for communicating direction information and command selections to the processors 220 and for controlling cursor movement on the display 266. The display 266 may provide a touch screen interface that may allow input to supplement or replace the communication of direction information and command selections by the pointing device 261 and/or keyboard 262.

The remote computing system 108 may perform a portion or each of the functions and methods described herein in response to the processors 220 executing one or more sequences of one or more instructions contained in a memory, such as the system memory 230. Such instructions may be read into the system memory 230 from another computer readable medium, such as a hard disk 241 or a removable media drive 242. The hard disk 241 may contain one or more data stores and data files used by embodiments described herein. Data store contents and data files may be encrypted to improve security. The processors 220 may also be employed in a multi-processing arrangement to execute the one or more sequences of instructions contained in system memory 230. In alternative embodiments, hard-wired circuitry may be used in place of or in combination with software instructions. Thus, embodiments are not limited to any specific combination of hardware circuitry and software.

As stated above, the remote computing system 108 may include at least one computer readable medium or memory for holding instructions programmed according to embodiments described herein and for containing data structures, tables, records, or other data described herein. The term computer readable medium as used herein refers to any non-transitory, tangible medium that participates in providing instructions to the processors 220 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 241 or removable media drive 242. Non-limiting examples of volatile media include dynamic memory, such as system memory 230. Non-limiting examples of transmission media include coaxial cables, copper wire, and fiber optics, including the wires that make up the bus 221. Transmission media may also take the form of acoustic or light waves, such as those generated during radio wave and IR data communications.

The computing environment 200 may further include the remote computing system 108 operating in a networked environment using logical connections to local computing device 106 and one or more other devices, such as a personal computer (laptop or desktop), mobile devices (e.g., patient mobile devices), a server, a router, a network PC, a peer device or other common network node, and typically includes many or all of the elements described above relative to the remote computing system 108. When used in a networking environment, remote computing system 108 may include modem 272 for establishing communications over the second network 120, such as the Internet. Modem 272 may be connected to system bus 221 via network interface 270, or via another appropriate mechanism.

The second network 120, as shown in FIGS. 1 and 2, may be any network or system generally known in the art, including the Internet, an intranet, a LAN, a WAN, a metropolitan area network (MAN), a direct connection or series of connections, a cellular telephone network, or any other network or medium capable of facilitating communication between computer system and other computers (e.g., local computing device 106).

Figure 3:
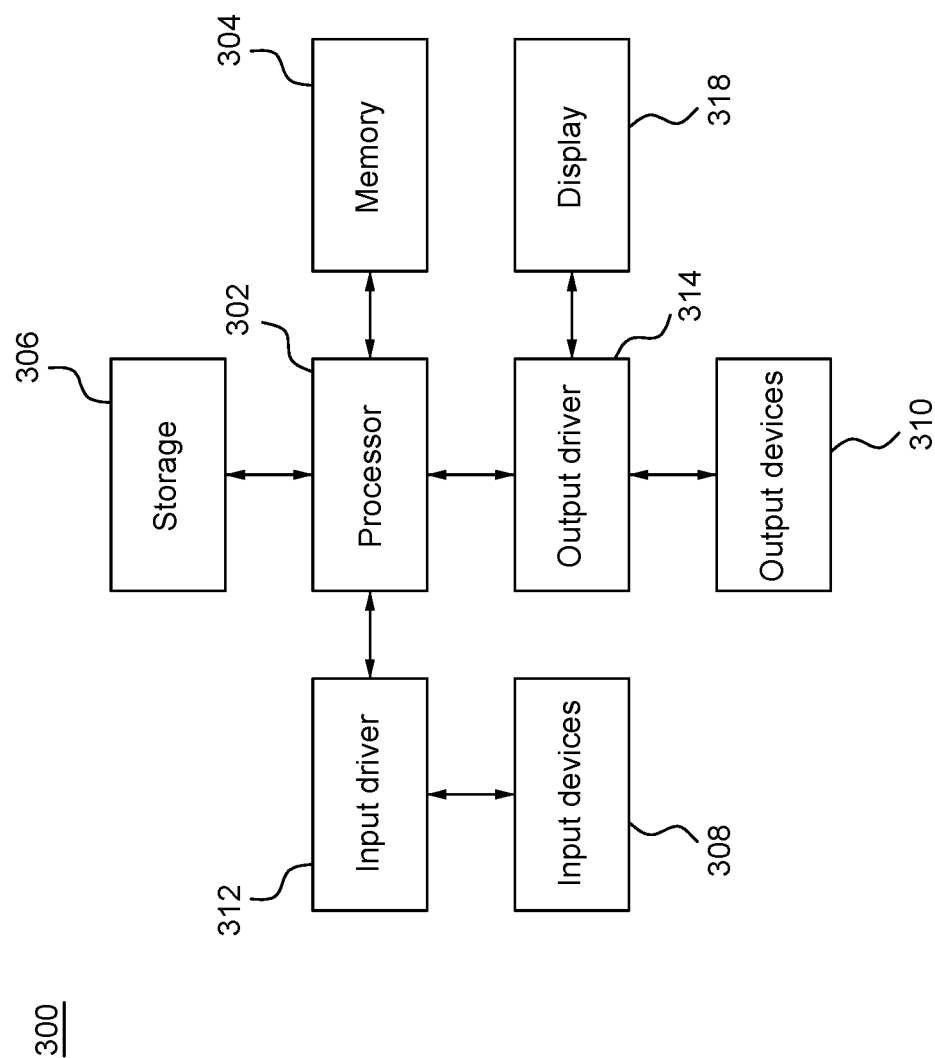
FIG. 3 is a block diagram of an exemplary device in which one or more features of the disclosure can be implemented in accordance with the subject matter of the present application.

FIG. 3 is a block diagram of an example device 300 in which one or more features of the disclosure can be implemented. The device 300 may be local computing device 106, for example. The device 300 may include, for example, a computer, a gaming device, a handheld device, a set-top box, a television, a mobile phone, or a tablet computer. The device 300 includes a processor 302, a memory 304, a storage device 306, one or more input devices 308, and one or more output devices 310. The device 300 can also optionally include an input driver 312 and an output driver 314. It is understood that the device 300 can include additional components not shown in FIG. 3 including an artificial intelligence accelerator.

In various alternatives, the processor 302 includes a CPU, a GPU, a CPU and GPU located on the same die, or one or more processor cores, wherein each processor core can be a CPU or a GPU. In various alternatives, the memory 304 is located on the same die as the processor 302, or is located separately from the processor 302. The memory 304 includes a volatile or non-volatile memory, for example, RAM, dynamic RAM, or a cache.

The storage device 306 includes a fixed or removable storage means, for example, a hard disk drive, a solid state drive, an optical disk, or a flash drive. The input devices 308 include, without limitation, a keyboard, a keypad, a touch screen, a touch pad, a detector, a microphone, an accelerometer, a gyroscope, a biometric scanner, or a network connection (e.g., a wireless LAN card for transmission and/or reception of wireless IEEE 802 signals). The output devices 310 include, without limitation, a display, a speaker, a printer, a haptic feedback device, one or more lights, an antenna, or a network connection (e.g., a wireless LAN card for transmission and/or reception of wireless IEEE 802 signals).

The input driver 312 communicates with the processor 302 and the input devices 308, and permits the processor 302 to receive input from the input devices 308. The output driver 314 communicates with the processor 302 and the output devices 310, and permits the processor 302 to send output to the output devices 310. It is noted that the input driver 312 and the output driver 314 are optional components, and that the device 300 will operate in the same manner if the input driver 312 and the output driver 314 are not present. The output driver 314 may include an accelerated processing device (APD) 316 which is coupled to a display device 318. The APD accepts compute commands and graphics rendering commands from processor 302, processes those compute and graphics rendering commands, and provides pixel output to display device 318 for display. As described in further detail below, the APD 316 includes one or more parallel processing units to perform computations in accordance with a single-instruction-multiple-data (SIMD) paradigm. Thus, although various functionality is described herein as being performed by or in conjunction with the APD 316, in various alternatives, the functionality described as being performed by the APD 316 is additionally or alternatively performed by other computing devices having similar capabilities that are not driven by a host processor (e.g., processor 302) and provides graphical output to a display device 318. For example, it is contemplated that any processing system that performs processing tasks in accordance with a SIMD paradigm may perform the functionality described herein. Alternatively, it is contemplated that computing systems that do not perform processing tasks in accordance with a SIMD paradigm performs the functionality described herein.

Figure 4:
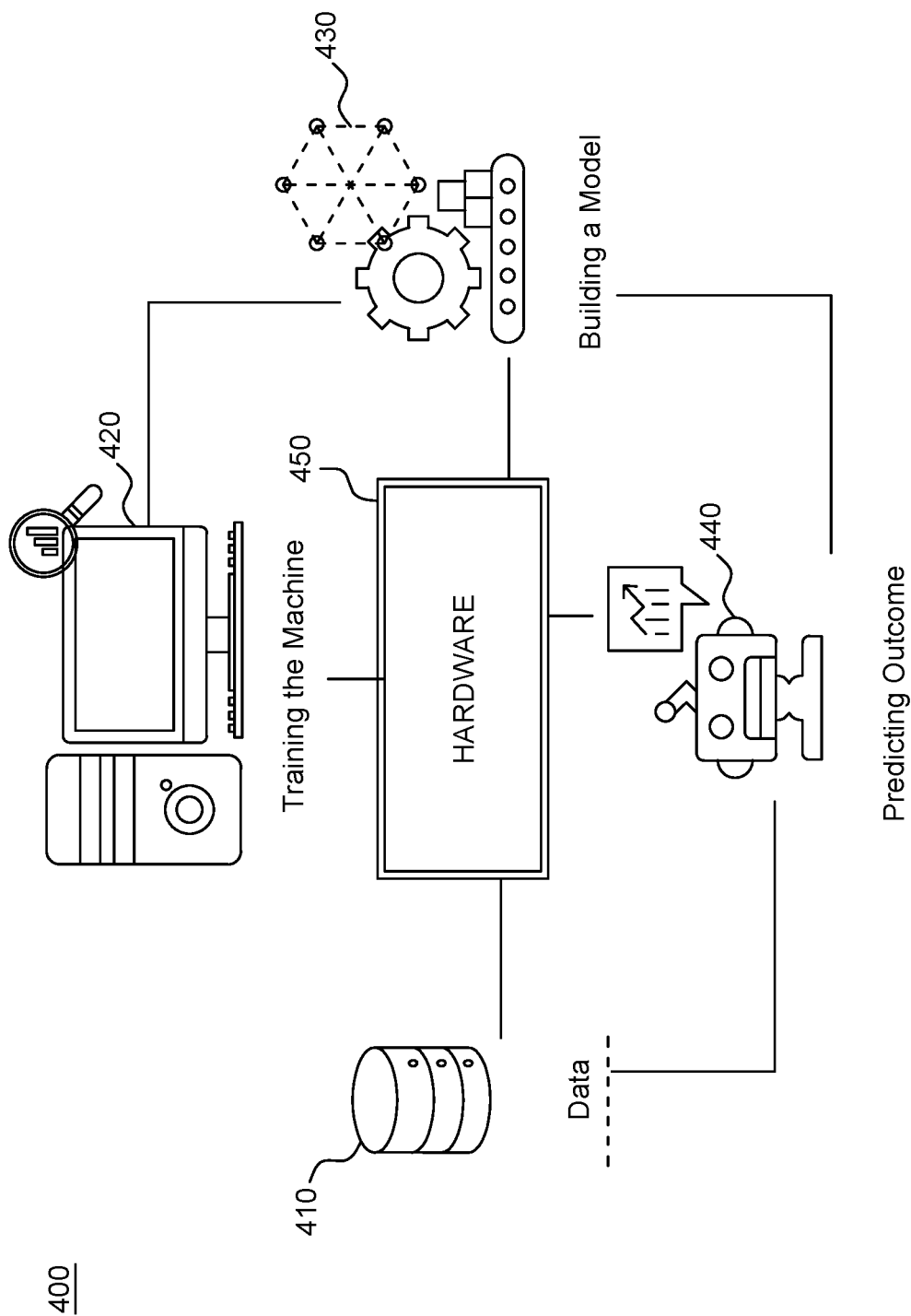
FIG. 4 illustrates a graphical depiction of an artificial intelligence system incorporating the example device of FIG. 3 in accordance with the subject matter of the present application.

FIG. 4 illustrates a functional graphical depiction of an artificial intelligence system 400 incorporating the example device of FIG. 3. System 400 includes data 410, a machine 420, a model 430, a plurality of predicted outcomes 440 and underlying hardware 450. System 400 operates by using the data 410 to train the machine 420 while building a model 430 to enable a plurality of outcomes 440 to be predicted. The system 400 may operate with respect to hardware 450. In such a configuration, the data 410 may be related to hardware 450 and may originate with the monitoring and processing apparatus 102, for example. For example, the data 410 may be on-going data, or output data associated with hardware 450. The machine 420 may operate as the controller or data collection associated with the hardware 450, or be associated therewith. The model 430 may be configured to model the operation of hardware 450 and model the data 410 collected from hardware 450 in order to predict the outcome achieved by hardware 450. Using the predicted outcome 440, hardware 450 may be configured to provide a certain desired outcome 440 from hardware 450.

Figure 5:
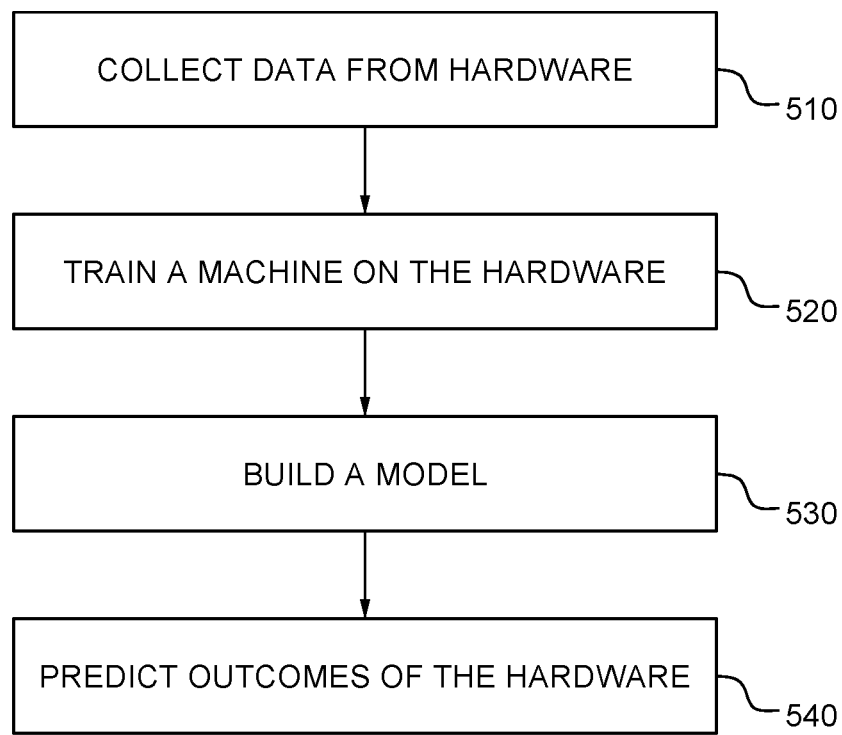
FIG. 5 illustrates a method performed in the artificial intelligence system of FIG. 4 in accordance with the subject matter of the present application.

FIG. 5 illustrates a general method 500 performed in the artificial intelligence system of FIG. 4. Method 500 includes collecting data from the hardware at 510. This data may include currently collected, historical or other data from the hardware, or various combinations thereof. For example, this data may include measurements during a surgical procedure and may be associated with the outcome of the procedure. For example, the temperature of a heart may be collected and correlated with the outcome of a heart procedure.

At 520, method 500 includes training a machine on the hardware. The training may include an analysis and correlation of the data collected in 510. For example, in the case of the heart, the data of temperature and outcome may be trained to determine if a correlation or link exists between the temperature of the heart during the procedure and the outcome.

At 530, method 500 includes building a model on the data associated with the hardware. Building a model may include physical hardware or software modeling, algorithmic modeling and the like, as will be described below. This modeling may seek to represent the data that has been collected and trained.

At 540, method 500 includes predicting the outcomes of the model associated with the hardware. This prediction of the outcome may be based on the trained model. For example, in the case of the heart, a temperature of 97.7° F.-100.2° F. during the procedure produces a positive result from the procedure and the outcome can be predicted in a given procedure based on the temperature of the heart during the procedure. While this model is rudimentary, it is provided for exemplary purposes and to increase understanding of the present disclosure.

The present system and method operate to train the machine, build the model and predict outcomes using algorithms. These algorithms may be used to solve the trained model and predict outcomes associated with the hardware. These algorithms may be divided generally into classification, regression and clustering algorithms.

For example, a classification algorithm is used in the situation where the dependent variable, which is the variable being predicted, is divided into classes and predicting a class, the dependent variable, for a given input. Thus, a classification algorithm is used to predict an outcome, from a set number of fixed, predefined outcomes. A classification algorithm may include naive Bayes algorithms, decision trees, random forest classifiers, logistic regressions, support vector machines (SVMs) and K Nearest Neighbors (KNN).

Generally, a naive Bayes algorithm follows the Bayes theorem, and follows a probabilistic approach. As would be understood, other probabilistic-based algorithms may also be used, and generally operate using similar probabilistic principles to those described below for the exemplary naive Bayes algorithm.

FIG. 6 illustrates an example of the probabilities of a naive Bayes calculation. The probability approach of Bayes theorem essentially means, that instead of jumping straight into the data, the algorithm has a set of prior probabilities for each of the classes for the target. After the data is entered, the naive Bayes algorithm may update the prior probabilities to form a posterior probability. This is given by the formula:

$$\text{posterior} = \frac{\text{prior} \times \text{likelihood}}{\text{evidence}}$$

This naive Bayes algorithm, and Bayes algorithms generally, may be useful when needing to predict whether an input belongs to a given list of n classes or not. The probabilistic approach may be used because the probabilities for all the n classes will be quite low.

For example, as illustrated in FIG. 6, a person playing golf, which depends on factors including, without limitation, the weather outside shown in a first data set 610. The first data set 610 illustrates the weather in a first column and an outcome of playing associated with that weather in a second column. In the frequency table 620 the frequencies with which certain events occur are generated. In frequency table 620, the frequency of a person playing or not playing golf in each of the weather conditions is determined. From there, a likelihood table is compiled to generate initial probabilities. For example, the probability of the weather being overcast is 0.29 while the general probability of playing is 0.64.

The posterior probabilities may be generated from the likelihood table 630. These posterior probabilities may be configured to answer questions about weather conditions and whether golf is played in those weather conditions. For example, the probability of it being sunny outside and golf being played may be set forth by the Bayesian formula:

$$P(\text{Yes}|\text{Sunny})=P(\text{Sunny}|\text{Yes})*P(\text{Yes})/P(\text{Sunny})$$

According to likelihood table 630:

$$P(\text{Sunny}|\text{Yes})=3/9=0.33,$$

$$P(\text{Sunny})=5/14=0.36,$$

$$P(\text{Yes})=9/14=0.64.$$

Therefore, the P(Yes|Sunny)=0.33*0.64/0.36 or approximately 0.60 (60%).

Generally, a decision tree is a flowchart-like tree structure where each external node denotes a test on an attribute and each branch represents the outcome of that test. The leaf nodes contain the actual predicted labels. The decision tree begins from the root of the tree with attribute values being compared until a leaf node is reached. A decision tree can be used as a classifier when handling high dimensional data and when little time has been spent behind data preparation. Decision trees may take the form of a simple decision tree, a linear decision tree, an algebraic decision tree, a deterministic decision tree, a randomized decision tree, a nondeterministic decision tree, and a quantum decision tree. An exemplary decision tree is provided below in FIG. 7.

Figure 7:
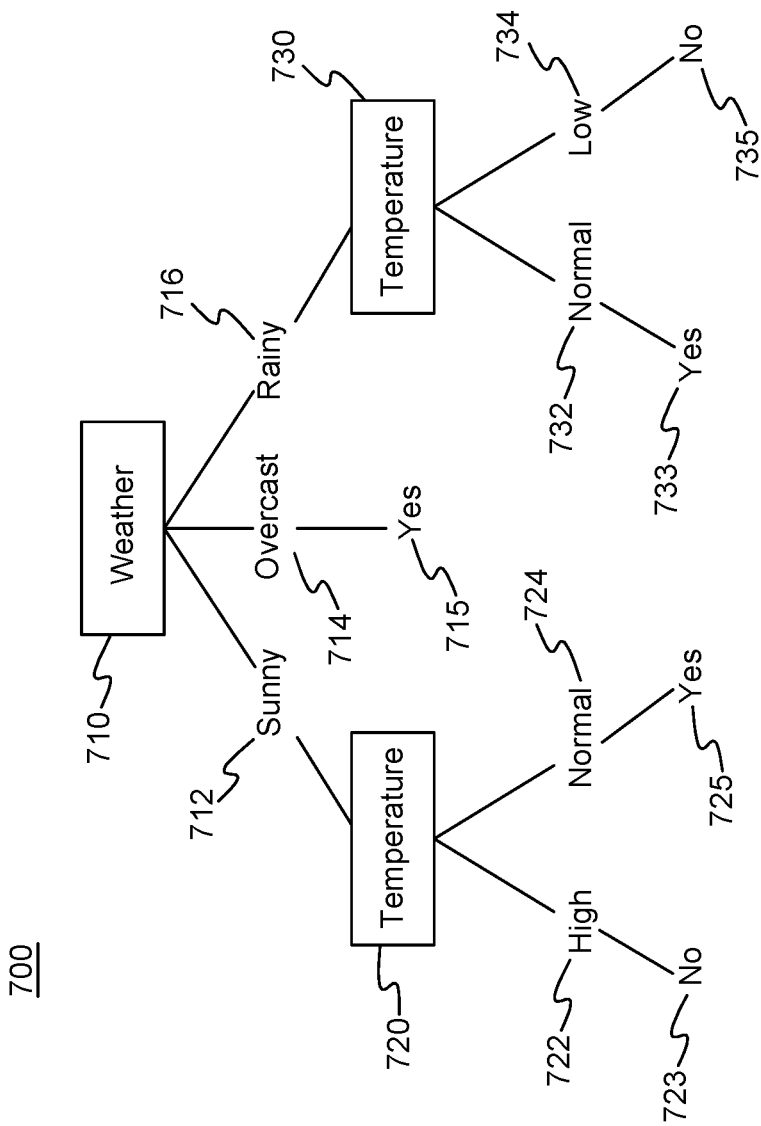
FIG. 7 illustrates an exemplary decision tree in accordance with the subject matter of the present application.

FIG. 7 illustrates a decision tree 700, along the same structure as the Bayes example above, in deciding whether to play golf. In the decision tree, the first node 710 examines the weather providing sunny 712, overcast 714, and rain 716 as the choices to progress down the decision tree. If the weather is sunny, the leg of the tree is followed to a second node 720 examining the temperature. The temperature at node 720 may be high 722 or normal 724, in this example. If the temperature at node 720 is high 722, then the predicted outcome of "No" 723 golf occurs. If the temperature at node 720 is normal 724, then the predicted outcome of "Yes" 725 golf occurs.

Further, from the first node 710, if the weather overcast 714, then the predicted outcome of "Yes" 715 golf occurs.

From the first node 710, an outcome of rain 716 results in the third node 730 (again) examining temperature. If the temperature at third node 730 is normal 732, then "Yes" 733 golf is played. If the temperature at third node 730 is low 734, then "No" 735 golf is played.

From this decision tree, a golfer plays golf if the weather is overcast 715, in normal temperature sunny weather 725, and in normal temperature rainy weather 733, while the golfer does not play if there are sunny high temperatures 723 or low rainy temperatures 735.

A random forest classifier is a committee of decision trees, where each decision tree has been fed a subset of the attributes of data and predicts on the basis of that subset. The mode of the actual predicted values of the decision trees are considered to provide an ultimate random forest answer. The random forest classifier, generally, alleviates overfitting, which is present in a standalone decision tree, leading to a much more robust and accurate classifier.

Figure 8:
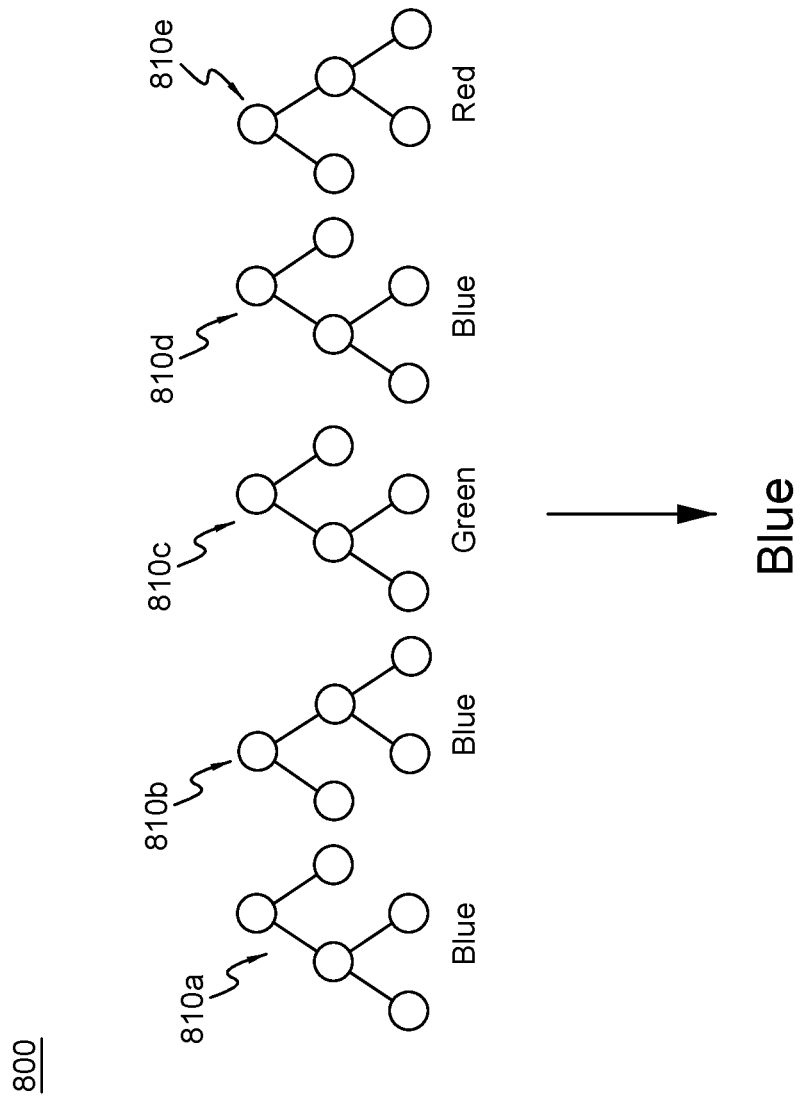
FIG. 8 illustrates an exemplary random forest classifier in accordance with the subject matter of the present application.

FIG. 8 illustrates an exemplary random forest classifier 800 for classifying the color of a garment. As illustrated in FIG. 8, the random forest classifier 800 includes five decision trees 810*a*, 810*b*, 810*c*, 810*d*, and 810*e* (collectively or generally referred to as decision trees 810). Each of the trees is designed to classify the color of the garment. A discussion of each of the trees and decisions made is not provided, as each individual tree generally operates as the decision tree of FIG. 7. In the illustration, three (810*a*, 810*b*, 810*d*) of the five trees determines that the garment is blue, while one determines the garment is green (810*c*) and the remaining tree determines the garment is red (810*e*). The random forest takes these actual predicted values of the five trees and calculates the mode of the actual predicted values to provide random forest answer that the garment is blue.

Logistic regression is another algorithm for binary classification tasks. Logistic regression is based on the logistic function, also called the sigmoid function. This S-shaped curve can take any real-valued number and map it between 0 and 1 asymptotically approaching those limits. The logistic model may be used to model the probability of a certain class or event existing such as pass/fail, win/lose, alive/dead or healthy/sick. This can be extended to model several classes of events such as determining whether an image contains a cat, dog, lion, etc. Each object being detected in the image would be assigned a probability between 0 and 1 with the sum of the probabilities adding to one.

In the logistic model, the log-odds (the logarithm of the odds) for the value labeled "1" is a linear combination of one or more independent variables ("predictors"); the independent variables can each be a binary variable (two classes, coded by an indicator variable) or a continuous variable (any real value). The corresponding probability of the value labeled "1" can vary between 0 (certainly the value "0") and 1 (certainly the value "1"), hence the labeling; the function that converts log-odds to probability is the logistic function, hence the name. The unit of measurement for the log-odds scale is called a logit, from logistic unit, hence the alternative names. Analogous models with a different sigmoid function instead of the logistic function can also be used, such as the probit model; the defining characteristic of the logistic model is that increasing one of the independent variables multiplicatively scales the odds of the given outcome at a constant rate, with each independent variable having its own parameter; for a binary dependent variable this generalizes the odds ratio.

In a binary logistic regression model, the dependent variable has two levels (categorical). Outputs with more than two values are modeled by multinomial logistic regression and, if the multiple categories are ordered, by ordinal logistic regression (for example the proportional odds ordinal logistic model). The logistic regression model itself simply models probability of output in terms of input and does not perform statistical classification (it is not a classifier), though it can be used to make a classifier, for instance by choosing a cutoff value and classifying inputs with probability greater than the cutoff as one class, below the cutoff as the other; this is a common way to make a binary classifier.

Figure 9:
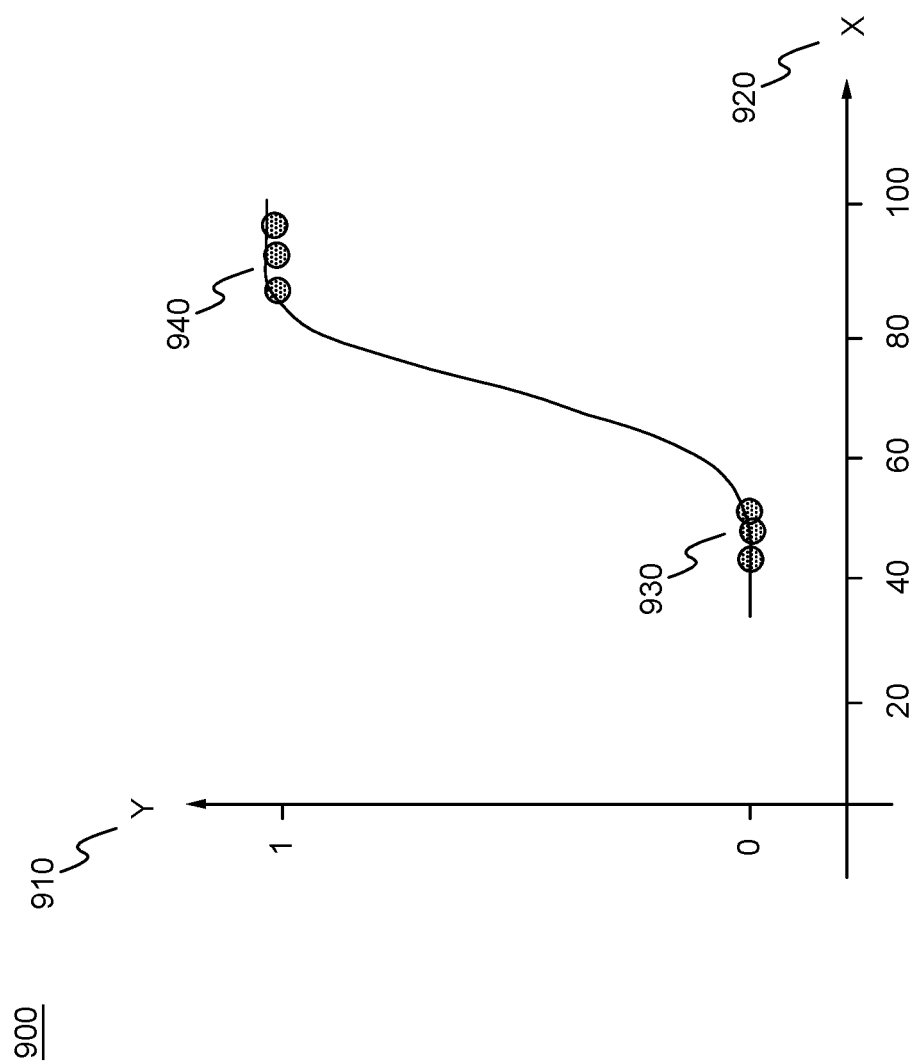
FIG. 9 illustrates an exemplary logistic regression in accordance with the subject matter of the present application.

FIG. 9 illustrates an exemplary logistic regression 900. This exemplary logistic regression enables the prediction of an outcome based on a set of variables. For example, based on a person's grade point average, and outcome of being accepted to a school may be predicted. The past history of grade point averages and the relationship with acceptance enables the prediction to occur. The logistic regression 900 enables the analysis of the grade point average variable 920 to predict the outcome 910 defined by 0 to 1. At the low end 930 of the S-shaped curve, the grade point average 920 predicts an outcome 910 of not being accepted. While at the high end 940 of the S-shaped curve, the grade point average 920 predicts an outcome 910 of being accepted. Logistic regression may be used to predict house values, customer lifetime value in the insurance sector, etc.

A SVM may be used to sort the data with the margins between two classes as far apart as possible. This is called maximum margin separation. The SVM may account for the support vectors while plotting the hyperplane, unlike linear regression which uses the entire dataset for that purpose.

Figure 10:
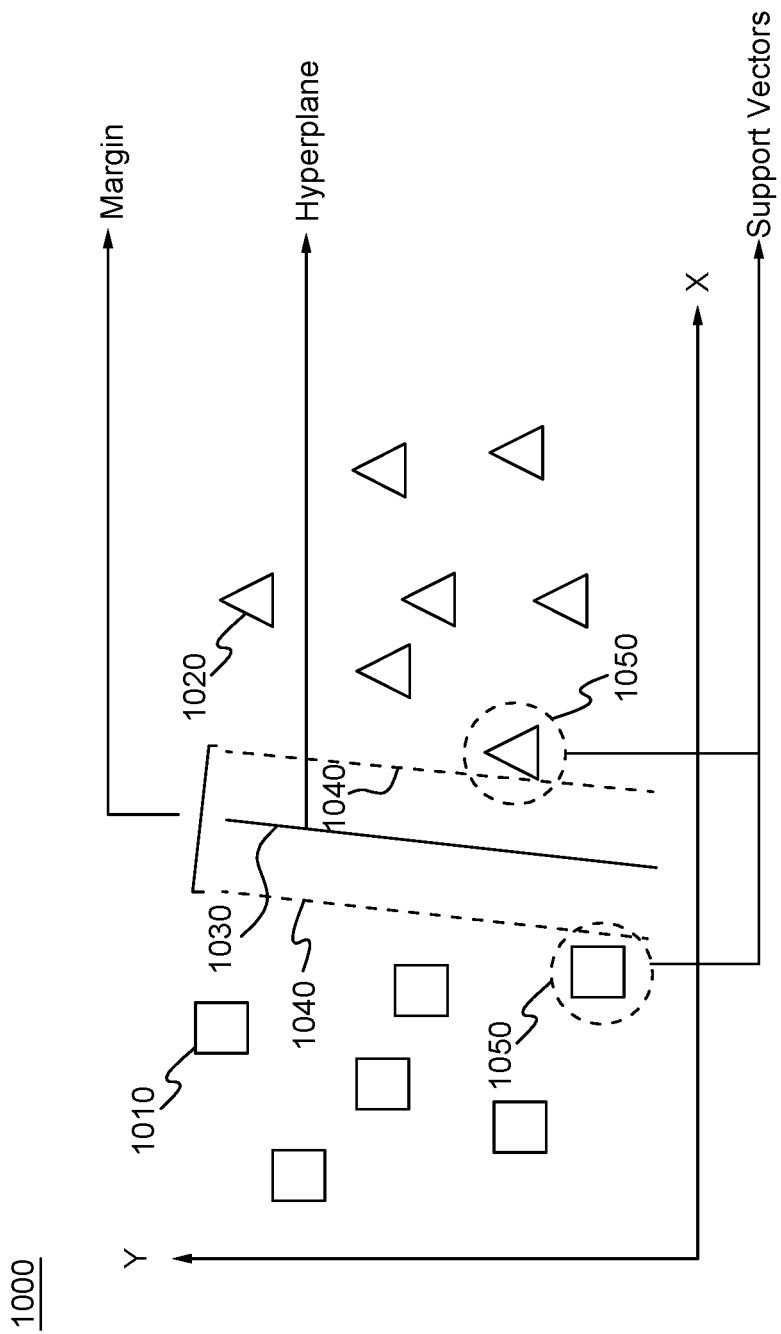
FIG. 10 illustrates an exemplary support vector machine (SVM) in accordance with the subject matter of the present application.

FIG. 10 illustrates an exemplary SVM 1000. In the exemplary SVM 1000, data may be classified into two different classes represented as squares 1010 and triangles 1020. SVM 1000 operates by drawing a random hyperplane 1030. This hyperplane 1030 is monitored by comparing the distance (illustrated with lines 1040) between the hyperplane 1030 and the closest data points 1050 from each class. The closest data points 1050 to the hyperplane 1030 are known as support vectors. The hyperplane 1030 is drawn based on these support vectors 1050 and an optimum hyperplane has a maximum distance from each of the support vectors 1050. The distance between the hyperplane 1030 and the support vectors 1050 is known as the margin.

SVM 1000 may be used to classify data by using a hyperplane 1030, such that the distance between the hyperplane 1030 and the support vectors 1050 is maximum. Such an SVM 1000 may be used to predict heart disease, for example.

KNN refers to a set of algorithms that generally do not make assumptions on the underlying data distribution, and perform a reasonably short training phase. Generally, KNN uses many data points separated into several classes to predict the classification of a new sample point. Operationally, KNN specifies an integer N with a new sample. The N entries in the model of the system closest to the new sample are selected. The most common classification of these entries is determined and that classification is assigned to the new sample. KNN generally requires the storage space to increase as the training set increases. This also means that the estimation time increases in proportion to the number of training points.

In regression algorithms, the output is a continuous quantity so regression algorithms may be used in cases where the target variable is a continuous variable. Linear regression is a general example of regression algorithms. Linear regression may be used to gauge genuine qualities (cost of houses, number of calls, all out deals and so forth) in view of the consistent variable(s). A connection between the variables and the outcome is created by fitting the best line (hence linear regression). This best fit line is known as regression line and spoken to by a direct condition $Y=a*X+b$. Linear regression is best used in approaches involving a low number of dimensions.

Figure 11:
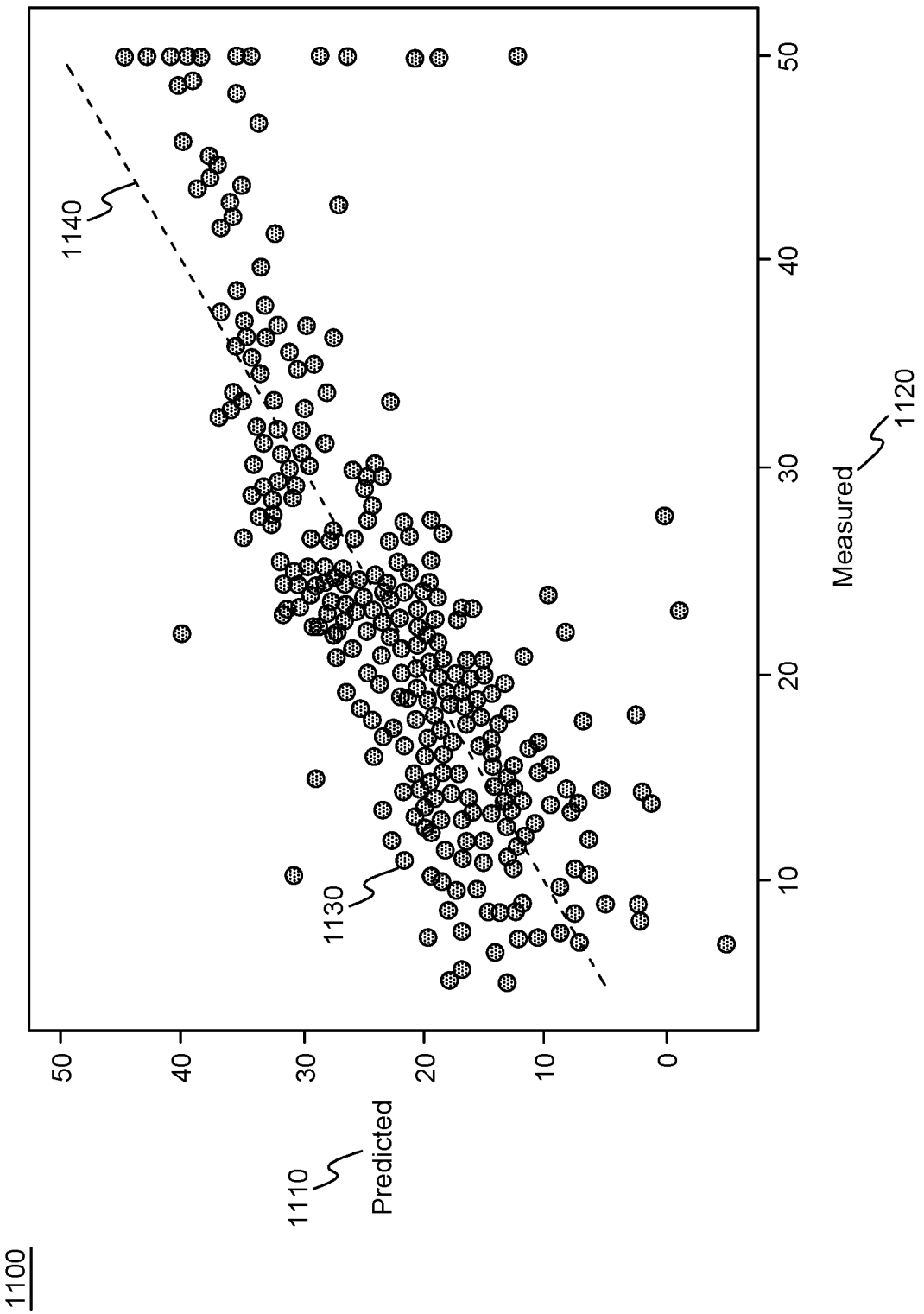
FIG. 11 illustrated an exemplary linear regression model in accordance with the subject matter of the present application.

FIG. 11 illustrates an exemplary linear regression model 1100. In this model, a predicted variable 1110 is modeled against a measured variable 1120. A cluster of instances of the predicted variable 1110 and measured variable 1120 are plotted as data points 1130. Data points 1130 are then fit with the best fit line 1140. Then the best fit line 1140 is used in subsequent predictions, given a measured variable 1120, the line 1140 is used to predict the predicted variable 1110 for that instance. Linear regression may be used to model and predict outcomes in a surgical procedure, performance of a financial portfolio, salary forecasting, real estate and in traffic in arriving at estimated time of arrival.

Clustering algorithms may also be used to model and train on a data set. In clustering, the input is assigned into two or more clusters based on feature similarity. Clustering algorithms generally learn the patterns and useful insights from data without any guidance. For example, clustering viewers into similar groups based on their interests, age, geography, etc. may be performed using unsupervised learning algorithms such as K-means clustering.

K-means clustering generally is regarded as a simple unsupervised learning approach. In K-means clustering, similar data points may be gathered together and bound in the form of a cluster. One method for binding the data points together is by calculating the centroid of the group of data points. In determining effective clusters in K-means clustering, the distance between each point from the centroid of the cluster is evaluated. Depending on the distance between the data point and the centroid, the data is assigned to the closest cluster. The goal of clustering is to determine the intrinsic grouping in a set of unlabeled data. The 'K' in K-means stands for the number of clusters formed. The number of clusters (basically the number of classes in which new instances of data may be classified) may be determined by the user. This determination may be performed using feedback and viewing the size of the clusters during training, for example.

K-means is used in cases where the data set has points which are distinct and well separated, otherwise, if the clusters are not separated the modeling may render the clusters inaccurate. Additionally, K-means may be avoided in cases where the data set contains a high number of outliers or the data set is non-linear.

Figure 12:
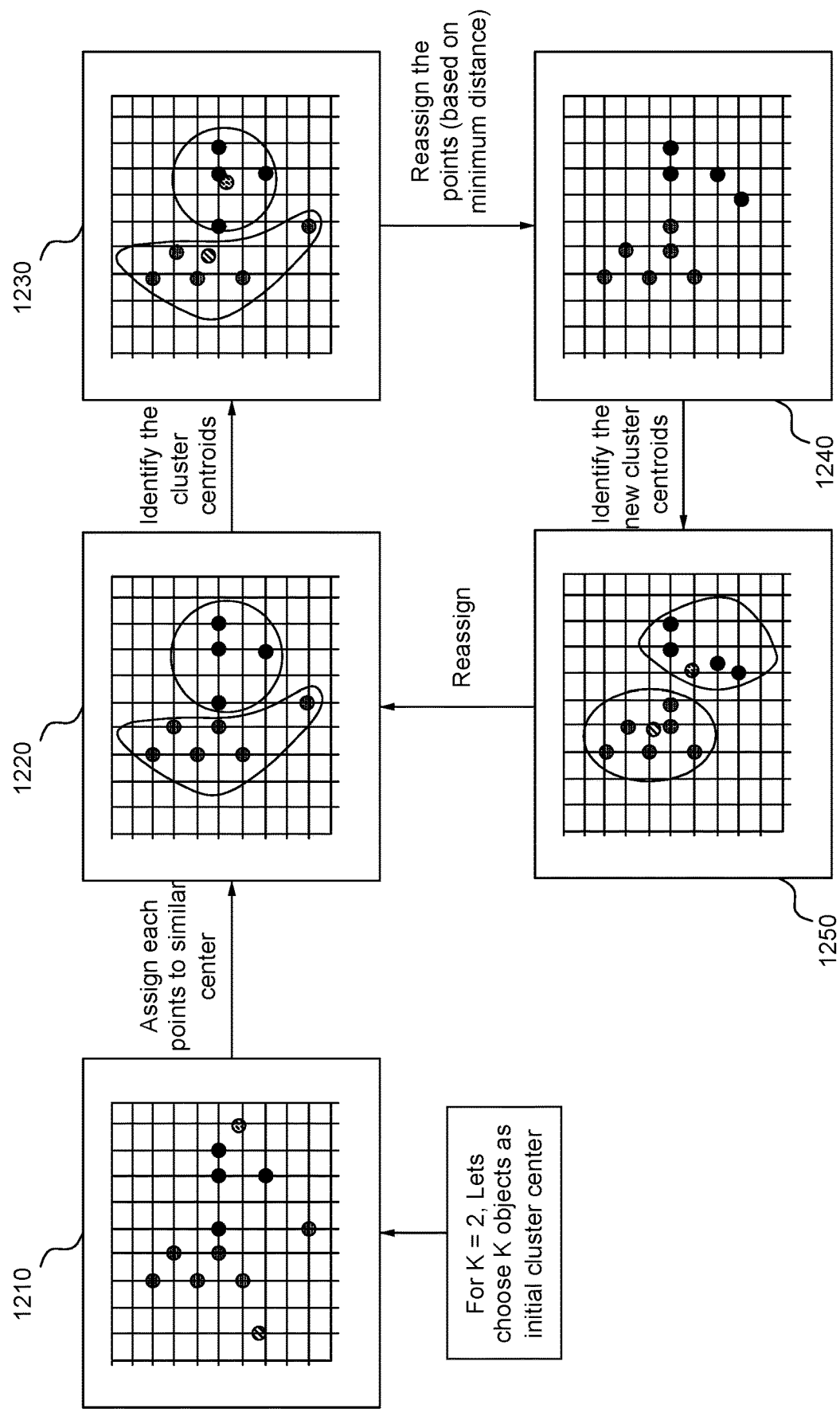
FIG. 12 illustrates an exemplary K-means clustering in accordance with the subject matter of the present application.

FIG. 12 illustrates K-means clustering. In K-means clustering, the data points are plotted and the K value is assigned. For example, for K=2 in FIG. 12, the data points are plotted as shown in depiction 1210. The points are then assigned to similar centers at 1220. The cluster centroids are identified as shown in 1230. Once centroids are identified, the points are reassigned to the cluster to provide the minimum distance between the data point to the respective cluster centroid as illustrated in 1240. Then a new centroid of the cluster may be determined as illustrated in depiction 1250. As the data pints are reassigned to a cluster and new cluster centroids formed, an iteration, or series of iterations, may occur to enable the clusters to be minimized in size and the centroid of the optimal centroid determined. Then as new data points are measured, the new data points may be compared with the centroid and cluster to identify with that cluster.

Ensemble learning algorithms may be used. These algorithms use multiple learning algorithms to obtain better predictive performance than could be obtained from any of the constituent learning algorithms alone. Ensemble learning algorithms perform the task of searching through a hypothesis space to find a suitable hypothesis that will make good predictions with a particular problem. Even if the hypothesis space contains hypotheses that are very well-suited for a particular problem, it may be very difficult to find a good hypothesis. Ensemble algorithms combine multiple hypotheses to form a better hypothesis. The term ensemble is usually reserved for methods that generate multiple hypotheses using the same base learner. The broader term of multiple classifier systems also covers hybridization of hypotheses that are not induced by the same base learner.

Evaluating the prediction of an ensemble typically requires more computation than evaluating the prediction of a single model, so ensembles may be thought of as a way to compensate for poor learning algorithms by performing a lot of extra computation. Fast algorithms such as decision trees are commonly used in ensemble methods, for example, random forests, although slower algorithms may benefit from ensemble techniques as well.

An ensemble is itself a supervised learning algorithm, because it can be trained and then used to make predictions. The trained ensemble, therefore, represents a single hypothesis. This hypothesis, however, is not necessarily contained within the hypothesis space of the models from which it is built. Thus, ensembles can be shown to have more flexibility in the functions they can represent. This flexibility can, in theory, enable them to over-fit the training data more than a single model would, but in practice, some ensemble techniques (especially bagging) tend to reduce problems related to over-fitting of the training data.

Empirically, ensemble algorithms tend to yield better results when there is a significant diversity among the models. Many ensemble methods, therefore, seek to promote diversity among the models they combine. Although non-intuitive, more random algorithms (like random decision trees) can be used to produce a stronger ensemble than very deliberate algorithms (like entropy-reducing decision trees). Using a variety of strong learning algorithms, however, has been shown to be more effective than using techniques that attempt to dumb-down the models in order to promote diversity.

The number of component classifiers of an ensemble has a great impact on the accuracy of prediction. A priori determining of ensemble size and the volume and velocity of big data streams make this even more crucial for online ensemble classifiers. A theoretical framework suggests that there are an ideal number of component classifiers for an ensemble such that having more or less than this number of classifiers would deteriorate the accuracy. The theoretical framework shows that using the same number of independent component classifiers as class labels gives the highest accuracy.

Figure 13:
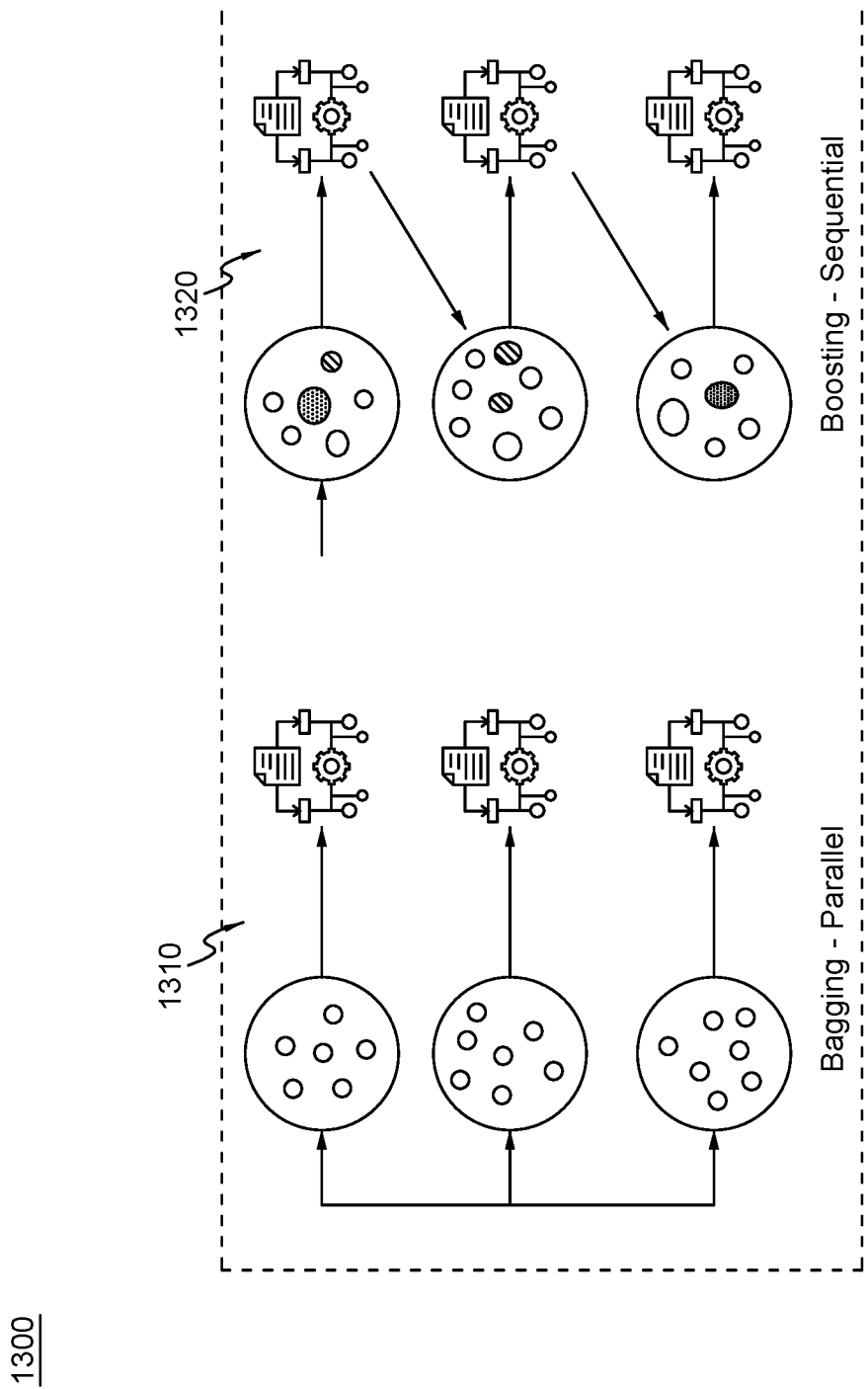
FIG. 13 illustrates an exemplary ensemble learning algorithm in accordance with the subject matter of the present application.

Some common types of ensembles include Bayes optimal classifier, bootstrap aggregating (bagging), boosting, Bayesian model averaging, Bayesian model combination, bucket of models and stacking. FIG. 13 illustrates an exemplary ensemble learning algorithm 1300 where bagging is being performed in parallel 1310 and boosting is being performed sequentially 1320.

During bagging, multiple subsets are created from an original dataset, with replacement. A base model is created on each of the subsets. The base models may run in parallel and be independent of each other. Final predictions may be determined by combining the predictions from all of the base models. Bagging may be an effective approach for reducing the variance of a model.

Boosting, on the other hand, is an iterative process, where each subsequent model attempts to correct errors of the previous model. Succeeding models are dependent on the previous model. First, a subset may be created from an original dataset. Initially, all data points are given equal weight. Next, a base model is created on this subset. This model is then used to make predictions on the whole dataset. Errors are calculated using actual values and predicted values. Observations which are incorrectly predicted are given higher weights. A second model is then created and predictions are made on the dataset. The second model attempts to correct the errors from the first model. Subsequent models are then be created, each correcting the errors of the previous model. The final model (i.e., strong learner) is a weighted mean of all of the previous models (i.e., weak learners). Therefore, boosting may be used to combine a number of weak learners to form a strong learner.

A neural network is a network or circuit of neurons, or in a modern sense, an artificial neural network (ANN), composed of artificial neurons or nodes. The connections of the biological neuron are modeled as weights. A positive weight reflects an excitatory connection, while negative values mean inhibitory connections. Inputs are modified by a weight and summed using a linear combination. An activation function may control the amplitude of the output. For example, an acceptable range of output is usually between 0 and 1, or it could be −1 and 1.

These artificial networks may be used for predictive modeling, adaptive control and applications and can be trained via a dataset. Self-learning resulting from experience can occur within networks, which can derive conclusions from a complex and seemingly unrelated set of information.

For completeness, a biological neural network is composed of a group or groups of chemically connected or functionally associated neurons. A single neuron may be connected to many other neurons and the total number of neurons and connections in a network may be extensive. Connections, called synapses, are usually formed from axons to dendrites, though dendrodendritic synapses and other connections are possible. Apart from the electrical signaling, there are other forms of signaling that arise from neurotransmitter diffusion.

Artificial intelligence, cognitive modeling, and neural networks are information processing paradigms inspired by the way biological neural systems process data. Artificial intelligence and cognitive modeling try to simulate some properties of biological neural networks. In the artificial intelligence field, ANNs have been applied successfully to speech recognition, image analysis and adaptive control, in order to construct software agents (in computer and video games) or autonomous robots.

A neural network, in the case of ANN or simulated neural network (SNN), is an interconnected group of natural or artificial neurons that uses a mathematical or computational model for information processing based on a connectionistic approach to computation. In most cases an ANN is an adaptive system that changes its structure based on external or internal information that flows through the network. In more practical terms neural networks are non-linear statistical data modeling or decision making tools. They can be used to model complex relationships between inputs and outputs or to find patterns in data.

An ANN involves a network of simple processing elements (artificial neurons) which can exhibit complex global behavior, determined by the connections between the processing elements and element parameters.

One classical type of ANN is the recurrent Hopfield network. The utility of ANN models lies in the fact that they can be used to infer a function from observations and also to use it. Unsupervised neural networks can also be used to learn representations of the input that capture the salient characteristics of the input distribution, and more recently, deep learning algorithms, which can implicitly learn the distribution function of the observed data. Learning in neural networks is particularly useful in applications where the complexity of the data or task makes the design of such functions by hand impractical.

Neural networks can be used in different fields. The tasks to which ANNs are applied tend to fall within the following broad categories: function approximation, or regression analysis, including time series prediction and modeling; classification, including pattern and sequence recognition, novelty detection and sequential decision making, data processing, including filtering, clustering, blind signal separation and compression.

Application areas of ANNs include nonlinear system identification and control (vehicle control, process control), game-playing and decision making (backgammon, chess, racing), pattern recognition (radar systems, face identification, object recognition), sequence recognition (gesture, speech, handwritten text recognition), medical diagnosis, financial applications, data mining (or knowledge discovery in databases, "KDD"), visualization and e-mail spam filtering. For example, it is possible to create a semantic profile of user's interests emerging from pictures trained for object recognition.

Figure 14:
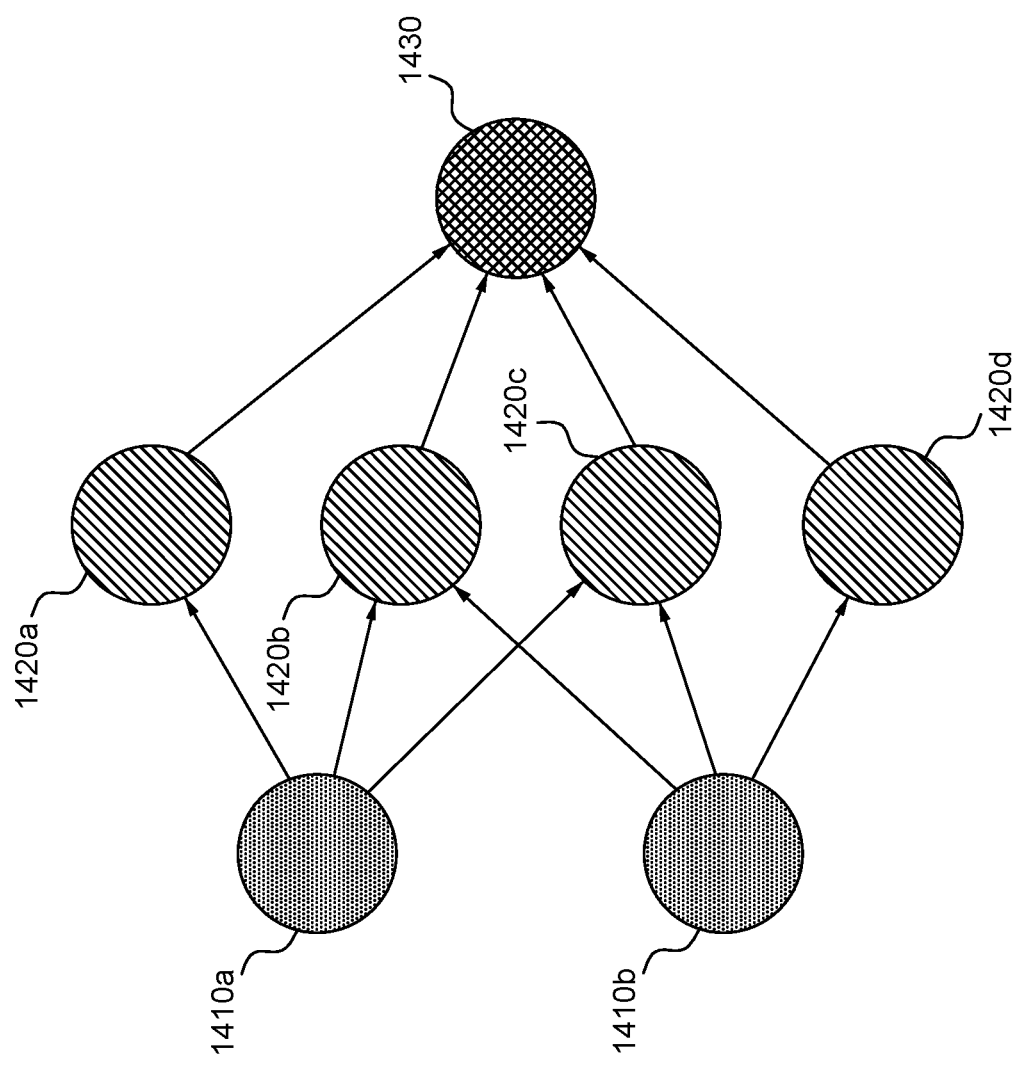
FIG. 14 illustrates an exemplary neural network in accordance with the subject matter of the present application.

FIG. 14 illustrates an exemplary neural network 1400. In the neural network 1400 there is an input layer represented by a plurality of inputs, such as 1410a and 1410b. The inputs 1410a, 1410b are provided to a hidden layer depicted as including nodes 1420a, 1420b, 1420c, 1420d. These nodes 1420a, 1420b, 1420c, 1420d are combined to produce an output 1430 in an output layer. The neural network performs simple processing via the hidden layer of simple processing elements, nodes 1420a, 1420b, 1420c, 1420d, which can exhibit complex global behavior, determined by the connections between the processing elements and element parameters.

Figure 15:
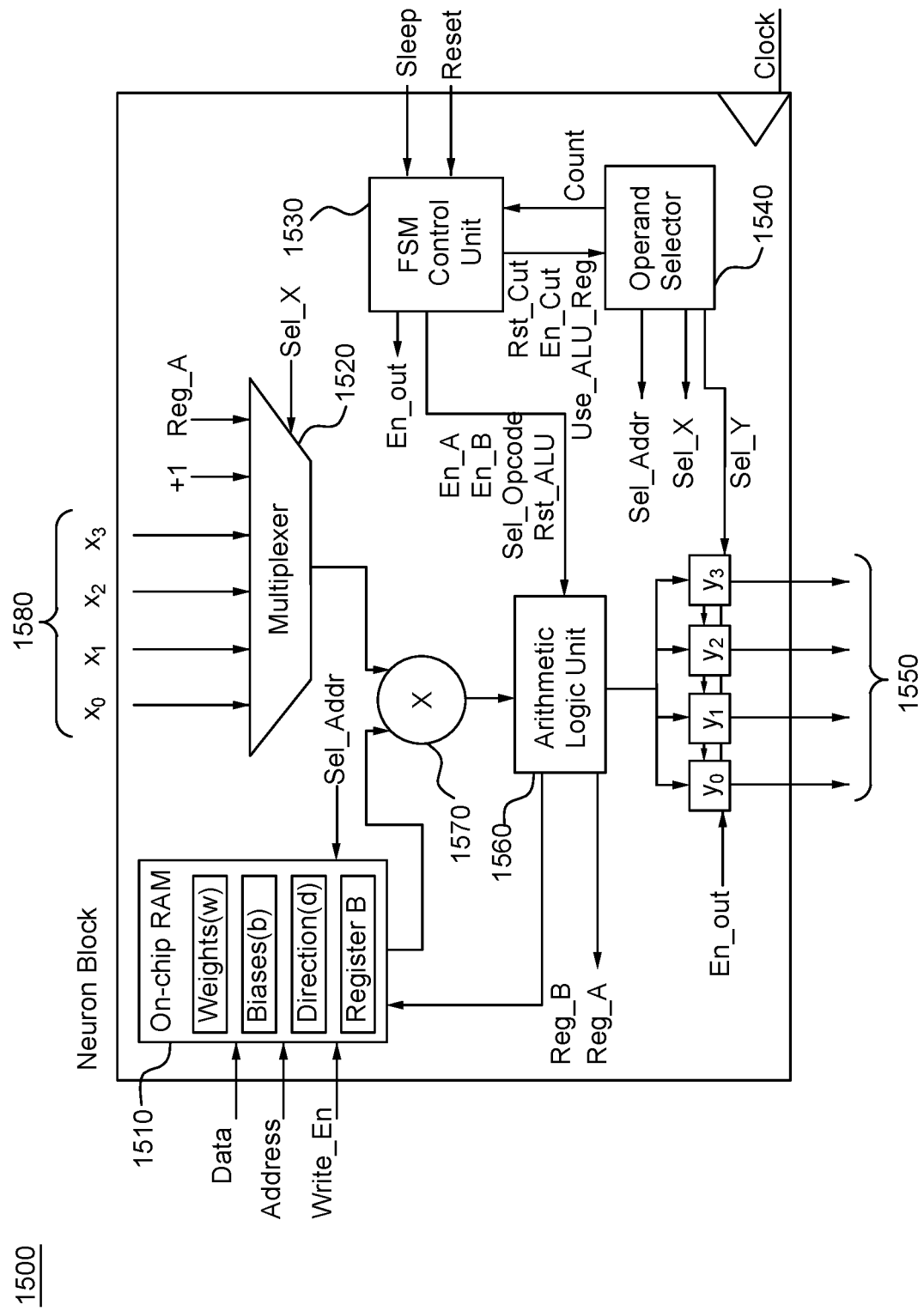
FIG. 15 illustrates a hardware based neural network in accordance with the subject matter of the present application.

Neural network 1400 may be implemented in hardware. In FIG. 15, a hardware based neural network 1500 is depicted. In an exemplary embodiment, and without limitation, hardware based neural network 1500 comprises a RAM 1510 which preferably includes weights, biases, direction, etc., multiplexer 1520, finite state machine (FSM) control unit 1530, operand selector 1540, arithmetic logic unit 1560, and multiplier unit 1570. Inputs 1580 are provided to the neural network 1500 and the neural network 1500 produces outputs 1550. For example, in the embodiment illustrated in FIG. 15, inputs 1580 are provided to multiplexer 1520 which forwards a selected input to the multiplexer unit 1570. Weights, biases, direction, etc. from the RAM 1510 are also forwarded to the multiplexer unit 1570. The multiplexer unit 1570 applies the weights, biases, direction, etc. to the selected input and forwards this result to the arithmetic logic unit 1560. The operand selector 1540 is configured to keep track of the number of the operand that is being multiplied. Information from the FSM control unit 1530 is also forwarded to the arithmetic logic unit 1560. The entire operation of the neuron block is controlled using the FSM control unit 1530. The arithmetic logical unit 1560 performs one of more arithmetic operations and produces outputs 1550.

Treatments for cardiac conditions such as cardiac arrhythmia often require obtaining a detailed mapping of cardiac tissue, chambers, veins, arteries and/or electrical pathways. Such mapping may be done via an EP investigation during which electrical potentials are detected spatially resolved with a mapping catheter introduced into the heart chamber.

This EP investigation, the so-called electro-anatomical (EA) mapping, thus provides 3D mapping data which can be displayed on a monitor. In many cases, the mapping function and a treatment function (e.g., ablation) are provided by a single catheter or group of catheters such that the mapping catheter also operates as a treatment (e.g., ablation) catheter at the same time.

Cardiac mapping may be implemented using one or more techniques. As an example of a first technique, cardiac mapping may be implemented by sensing an electrical property of heart tissue, for example local activation time (LAT), as a function of the precise location within the heart. The corresponding data may be acquired with one or more catheters that are advanced into the heart using catheters that have electrical and location sensors in their distal tips. As an example, location and electrical activity may be initially measured on about 10 to about 20 points on the interior surface of the heart. These data points may be generally sufficient to generate a preliminary reconstruction or map of the cardiac surface to a satisfactory quality. The preliminary map may be combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. Maps depicting such motion characteristics may be constructed when the trajectory information is sampled at a sufficient number of points in the heart.

Electrical activity at a point in the heart may be typically measured by advancing a catheter containing an electrical sensor at or near its distal tip to that point in the heart, contacting the tissue with the sensor and acquiring data at that point. Multiple-electrode catheters may be implemented using any applicable shape such as a linear catheter with multiple electrodes, a balloon catheter including electrodes dispersed on multiple spines that shape the balloon, a lasso or loop catheter with multiple electrodes, or any other applicable shape.

According to an example, a multi-electrode catheter may be advanced into a chamber of the heart. Anteroposterior (AP) and lateral fluorograms may be obtained to establish the position and orientation of each of the electrodes. Electrograms (EGMs) may be recorded from each of the electrodes in contact with a cardiac surface relative to a temporal reference such as the onset of the P-wave in sinus rhythm from a body surface ECG. The system, as further disclosed herein, may differentiate between those electrodes that register electrical activity and those that do not due to absence of close proximity to the endocardial wall. After initial EGMs are recorded, the catheter may be repositioned, and fluorograms and EGMs may be recorded again. An electrical map may then be constructed from iterations of the process above.

According to an example, cardiac mapping may be generated based on detection of intracardiac electrical potential fields. A non-contact technique to simultaneously acquire a large amount of cardiac electrical information may be implemented. For example, a catheter having a distal end portion may be provided with a series of sensor electrodes distributed over its surface and connected to insulated electrical conductors for connection to signal sensing and processing means. The size and shape of the end portion may be such that the electrodes are spaced substantially away from the wall of the cardiac chamber. Intracardiac potential fields may be detected during a single cardiac beat. According to an example, the sensor electrodes may be distributed on a series of circumferences lying in planes spaced from each other. These planes may be perpendicular to the major axis of the end portion of the catheter. At least two additional electrodes may be provided adjacent at the ends of the major axis of the end portion. As a more specific example, the catheter may include four circumferences with eight electrodes spaced equiangularly on each circumference. Accordingly, in this specific implementation, the catheter may include at least 34 electrodes (32 circumferential and 2 end electrodes).

According to another example, an EP cardiac mapping system and technique based on a non-contact and non-expanded multi-electrode catheter may be implemented. EGMs may be obtained with catheters having multiple electrodes (e.g., between 42 to 122 electrodes). According to this implementation, knowledge of the relative geometry of the probe and the endocardium may be obtained such as by an independent imaging modality such as transesophageal echocardiography. After the independent imaging, non-contact electrodes may be used to measure cardiac surface potentials and construct maps therefrom. This technique may include the following steps (after the independent imaging step): (a) measuring electrical potentials with a plurality of electrodes disposed on a probe positioned in the heart; (b) determining the geometric relationship of the probe surface and the endocardial surface; (c) generating a matrix of coefficients representing the geometric relationship of the probe surface and the endocardial surface; and (d) determining endocardial potentials based on the electrode potentials and the matrix of coefficients According to another example, a technique and apparatus for mapping the electrical potential distribution of a heart chamber may be implemented. An intra-cardiac (IC) multi-electrode mapping catheter assembly may be inserted into a patient's heart. The mapping catheter assembly may include a multi-electrode array with an integral reference electrode, or, preferably, a companion reference catheter. The electrodes may be deployed in the form of a substantially spherical array. The electrode array may be spatially referenced to a point on the endocardial surface by the reference electrode or by the reference catheter which is brought into contact with the endocardial surface. The preferred electrode array catheter may carry a number of individual electrode sites (e.g., at least 24). Additionally, this example technique may be implemented with knowledge of the location of each of the electrode sites on the array, as well as a knowledge of the cardiac geometry. These locations are preferably determined by a technique of impedance plethysmography.

According to another example, a process for measuring electrophysiologic data in a heart chamber may be implemented. The method may include, in part, positioning a set of active and passive electrodes into the heart, supplying current to the active electrodes, thereby generating an electric field in the heart chamber, and measuring the electric field at the passive electrode sites. The passive electrodes are contained in an array positioned on an inflatable balloon of a balloon catheter. In preferred embodiments, the array is said to have from 60 to 64 electrodes.

According to another example, cardiac mapping may be implemented using one or more ultrasound transducers. The ultrasound transducers may be inserted into a patient's heart and may collect a plurality of ultrasound slices (e.g., two dimensional or three-dimensional slices) at various locations and orientations within the heart. The location and orientation of a given ultrasound transducer may be known and the collected ultrasound slices may be stored such that they can be displayed at a later time. One or more ultrasound slices corresponding to the position of a probe (e.g., a treatment catheter) at the later time may be displayed and the probe may be overlaid onto the one or more ultrasound slices.

According to other examples, body patches and/or body surface electrodes may be positioned on or proximate to a patient's body. A catheter with one or more electrodes may be positioned within the patient's body (e.g., within the patient's heart) and the position of the catheter may be determined by a system based on signals transmitted and received between the one or more electrodes of the catheter and the body patches and/or body surface electrodes. Additionally, the catheter electrodes may sense biometric data (e.g., LAT values) from within the body of the patient (e.g., within the heart). The biometric data may be associated with the determined position of the catheter such that a rendering of the patient's body part (e.g., heart) may be displayed and may show the biometric data overlaid on a shape of the body part, as determined by the position of the catheter.

Figure 16:
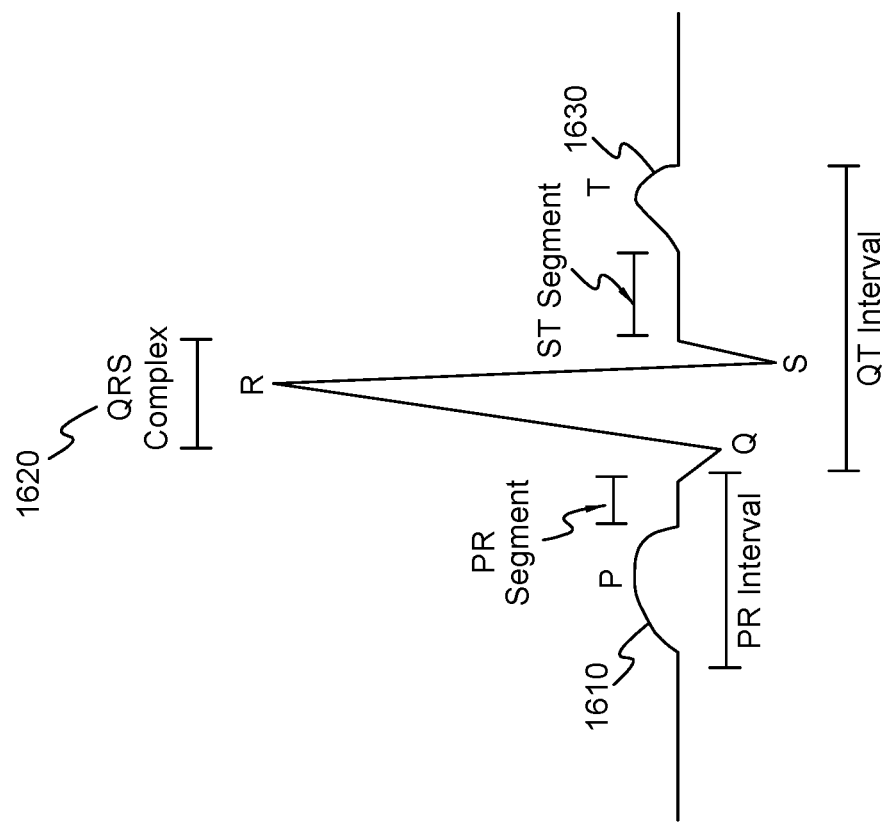
FIG. 16 shows an electrocardiogram (ECG) signal generated by contraction (depolarization) and relaxation (repolarization) of atrial and ventricular muscles of the heart in accordance with the subject matter of the present application.

Electrical signals such as ECG signals are often detected prior to and/or during a cardiac procedure. For example, ECG signals can be used to identify potential locations of a heart where arrhythmia causing signals originate from. Generally, an ECG is a signal that describes the electrical activity of the heart. ECG signals may also be used to map portions of a heart. An ECG signal is generated by contraction (depolarization) and relaxation (repolarization) of atrial and ventricular muscles of the heart. As shown by signal 1600 in FIG. 16, an ECG signal contains a P wave 1610 (due to atrial depolarization), a QRS complex 1620 (due to atrial repolarization and ventricular depolarization) and a T wave 1630 (due to ventricular repolarization). In order to record an ECG signal, electrodes may be placed at specific positions on the human body or can be positioned within a human body via a catheter. Artifacts (e.g., noise) are the unwanted signals that are merged with electronic signals such as ECG signals, and sometimes create obstacles for the diagnosis and/or treatment of a cardiac condition. Artifacts in electrical signals can be baseline wander, powerline interference, electromyogram (EMG) noise, power line noise, muscle noise, etc.

Additionally, biometric (e.g., biopotential) patient monitors may use surface electrodes to make measurements of bioelectric potentials such as ECG or electroencephalogram (EEG). The fidelity of these measurements is limited by the effectiveness of the connection of the electrode to the patient. The resistance of the electrode system to the flow of electric currents, known as the electric impedance, characterizes the effectiveness of the connection. Typically, the higher the impedance, the lower the fidelity of the measurement. Several mechanisms may contribute to lower fidelity.

Figure 17:
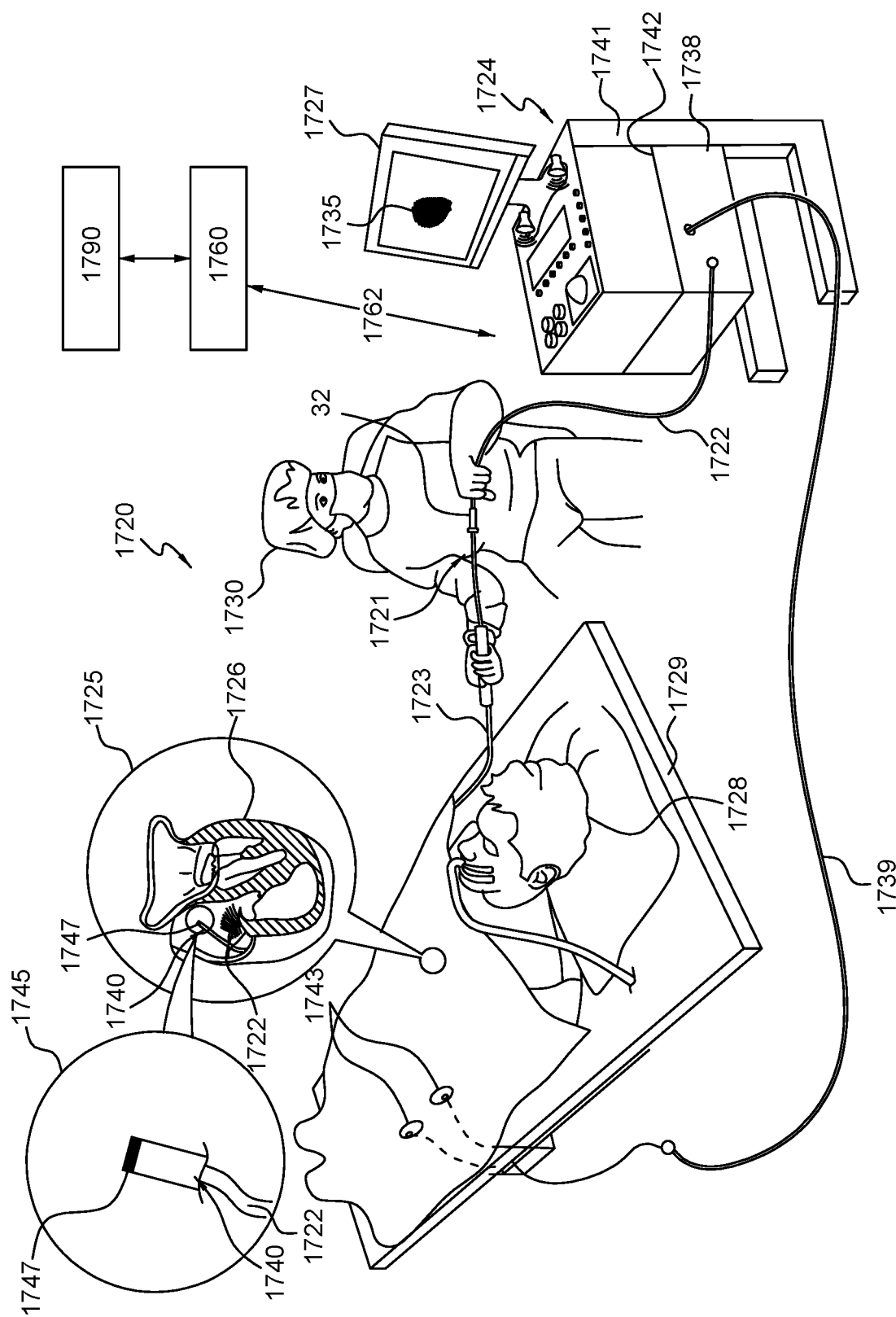
FIG. 17 illustrates an exemplary cardiac ablation system in which one or more features of the disclosed subject matter can be implemented in accordance with the subject matter of the present application.

FIG. 17 is a diagram of an exemplary system 1720 in which one or more features of the disclosure subject matter can be implemented. All or parts of system 1720 may be used to collect information for a training dataset and/or all or parts of system 1720 may be used to implement a trained model. System 1720 may include components, such as a catheter 1740, that are configured to damage tissue areas of an intra-body organ. The catheter 1740 may also be further configured to obtain biometric data including electronic signals. Although catheter 1740 is shown to be a point catheter, it will be understood that a catheter of any shape that includes one or more elements (e.g., electrodes) may be used to implement the embodiments disclosed herein. System 1720 includes a probe 1721, having shafts that may be navigated by a physician 1730 into a body part, such as heart 1726, of a patient 1728 lying on a table 1729. According to embodiments, multiple probes may be provided, however, for purposes of conciseness, a single probe 1721 is described in this example, but it will be understood that probe 1721 may represent multiple probes. As shown in FIG. 17, physician 1730 may insert shaft 1722 through a sheath 1723, while manipulating the distal end of the shafts 1722 using a manipulator near the proximal end of the catheter 1740 and/or deflection from the sheath 1723. As shown in an inset 1725, catheter 1740 may be fitted at the distal end of shafts 1722. Catheter 1740 may be inserted through sheath 1723 in a collapsed state and may be then expanded within heart 1726. Cather 1740 may include at least one ablation electrode 1747 and a catheter needle, as further described herein.

According to embodiments, catheter 1740 may be configured to ablate tissue areas of a cardiac chamber of heart 1726. Inset 1745 shows catheter 1740 in an enlarged view, inside a cardiac chamber of heart 1726. As shown, catheter 1740 may include at least one ablation electrode 1747 coupled onto the body of the catheter. According to other embodiments, multiple elements may be connected via splines that form the shape of the catheter 1740. One or more other elements (not shown) may be provided and may be any elements configured to ablate or to obtain biometric data and may be electrodes, transducers, or one or more other elements.

According to embodiments disclosed herein, the ablation electrodes, such as electrode 1747, may be configured to provide energy to tissue areas of an intra-body organ such as heart 1726. The energy may be thermal energy and may cause damage to the tissue area starting from the surface of the tissue area and extending into the thickness of the tissue area.

According to embodiments disclosed herein, biometric data may include one or more of LATs, electrical activity, topology, bipolar mapping, dominant frequency, impedance, or the like. The LAT may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequency that is prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 17, the probe 1721, and catheter 1740 may be connected to a console 1724. Console 1724 may include a processor 1741, such as a general-purpose computer, with suitable front end and interface circuits 1738 for transmitting and receiving signals to and from catheter, as well as for controlling the other components of system 1720. In some embodiments, processor 1741 may be further configured to receive biometric data, such as electrical activity, and determine if a given tissue area conducts electricity.

According to an embodiment, the processor may be external to the console 1724 and may be located, for example, in the catheter, in an external device, in a mobile device, in a cloud-based device, or may be a standalone processor.

As noted above, processor 1741 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 17 may be modified to implement the embodiments disclosed herein. The disclosed embodiments may similarly be applied using other system components and settings. Additionally, system 1720 may include additional components, such as elements for sensing electrical activity, wired or wireless connectors, processing and display devices, or the like.

According to an embodiment, a display 1727 connected to a processor (e.g., processor 1741) may be located at a remote location such as a separate hospital or in separate healthcare provider networks. Additionally, the system 1720 may be part of a surgical system that is configured to obtain anatomical and electrical measurements of a patient's organ, such as a heart, and performing a cardiac ablation procedure. An example of such a surgical system is the Carto® system sold by Biosense Webster.

The system 1720 may also, and optionally, obtain biometric data such as anatomical measurements of the patient's heart using ultrasound, computed tomography (CT), magnetic resonance imaging (MRI) or other medical imaging techniques known in the art. The system 1720 may obtain electrical measurements using catheters, ECGs or other sensors that measure electrical properties of the heart. The biometric data including anatomical and electrical measurements may then be stored in a memory 1742 of the mapping system 1720, as shown in FIG. 17. The biometric data may be transmitted to the processor 1741 from the memory 1742. Alternatively, or in addition, the biometric data may be transmitted to a server 1760, which may be local or remote, using a network 1762.

Network 1762 may be any network or system generally known in the art such as an intranet, a LAN, a WAN, a MAN, a direct connection or series of connections, a cellular telephone network, or any other network or medium capable of facilitating communication between the mapping system 1720 and the server 1760. The network 1762 may be wired, wireless or a combination thereof. Wired connections may be implemented using Ethernet, USB, RJ-11 or any other wired connection generally known in the art. Wireless connections may be implemented using Wi-Fi, WiMAX, and Bluetooth, IR, cellular networks, satellite or any other wireless connection methodology generally known in the art. Additionally, several networks may work alone or in communication with each other to facilitate communication in the network 1762.

In some instances, the server 1760 may be implemented as a physical server. In other instances, server 1762 may be implemented as a virtual server a public cloud computing provider (e.g., Amazon Web Services (AWS)®).

According to an exemplary embodiment, the server 1760 can be implemented as, or in communication with, a processor storing a machine learning algorithm, such as a neural network 1790. In another embodiment, the neural network 1790 can be implemented in console 1724. For example, and without limitation, neural network 1790 may be implemented on one or multiple CPU processors, on one or multiple GPU processors, on one or multiple FPGA chips, or on an ASIC dedicated to perform deep learning calculations, such as the Intel® Nervana™ Neural Network Processor. According to an exemplary embodiment, neural network 1790 can be located, without limitation, in the medical procedure room, on a server or processor in a hospital or medical facility, on a remote server or processor, or in the cloud.

Control console 1724 may be connected, by a cable 1739, to body surface electrodes 1743, which may include adhesive skin patches that are affixed to the patient 1728. The processor, in conjunction with a current tracking module, may determine position coordinates of the catheter 1740 inside the body part (e.g., heart 1726) of a patient. The position coordinates may be based on impedances or electromagnetic fields measured between the body surface electrodes 1743 and the electrode 1747 or other electromagnetic components of the catheter 1740. Additionally, or alternatively, location pads may be located on the surface of table 1729 and may be separate from the table 1729.

Processor 1741 may include real-time noise reduction circuitry typically configured as a field programmable gate array (FPGA), followed by an analog-to-digital (A/D) ECG or EMG signal conversion integrated circuit. The processor 1741 may pass the signal from an A/D ECG or EMG circuit to another processor and/or can be programmed to perform one or more functions disclosed herein.

Control console 1724 may also include an input/output (I/O) communications interface that enables the control console to transfer signals from, and/or transfer signals to electrode 1747.

During a procedure, processor 1741 may facilitate the presentation of a body part rendering 1735 to physician 1730 on a display 1727, and store data representing the body part rendering 1735 in a memory 1742. Memory 1742 may comprise any suitable volatile and/or non-volatile memory, such as RAM or a hard disk drive. In some embodiments, the physician 1730 may be able to manipulate a body part rendering 1735 using one or more input devices such as a touch pad, a mouse, a keyboard, a gesture recognition apparatus, or the like. For example, an input device may be used to change the position of catheter 1740 such that rendering 1735 is updated. In alternative embodiments, display 1727 may include a touchscreen that can be configured to accept inputs from physician 1730, in addition to presenting a body part rendering 1735.

The processor 1741 may acquire a plurality of electrical signals obtained by the catheter 1740, ECGs other sensors that measure electrical properties of the heart, as described above. The processor 1741 may apply an algorithm for optimal heartbeat selection. In some embodiments, the algorithm may comprise dynamic filtering of the electrical signals to determine which of the electrical signals are integrated as a "point" in a "point cloud" which represents the desired anatomical structure, such as a chamber of the heart.

The algorithm may comprise a plurality of filters. The filters may include, but are not limited to: position stability, inner distance, catheter filter, cycle length, cycle length stability, ventricle activity, position density, respiration, pattern matching, LAT, LAT stability, unipolar slope, bipolar voltage, tissue proximity indicator (TPI), fractionation stability, and noise level. However, this list is not exhaustive and the dynamic filters may utilize other parameters.

In some embodiments, the algorithm may comprise two phases of filtering: Phase One and Phase Two. In Phase One, one or more first filters may be applied to all of the collected electrical signals. The first filters may include, but are not limited to: position stability, inner distance, catheter filter, cycle length, ventricle activity, position density, respiration cycle indication, and pattern matching. If the electrical signal meets certain criteria in Phase One, one or more second filters may be applied at Phase Two. The second filters may include, but are not limited to: relative LAT stability, slope of a unipolar signal, bipolar voltage, TPI, and fractionation stability.

In some embodiments, one or more parameters may be calculated in Phase Two depending on the characteristics of the signal. For example, in Phase Two the signals may be analyzed to determine if they have LAT. Further, the bipolar voltage may be calculated and analyzed. The signals may also be analyzed to determine whether the electrodes are in proximity with the tissue. The force value (in grams) may also be analyzed. The relative position of the point inside the respiration cycle may also be analyzed. In some embodiments, the algorithm determines if the bipolar voltage is high or low. For example, a signal may be considered as having a "high" bipolar voltage if the bipolar voltage is greater than or equal to 0.1 mV and "low" bipolar voltage if the bipolar voltage is less than 0.1 mV. However, as will be appreciated by one having ordinary still in the art, the bipolar voltage "high" and "low" thresholds may vary based upon many factors, which may be specific to the particular patient or not. The threshold value may be entered to the system by the physician (for example via a graphical user interface) during the case. If it is determined that a signal with LAT has a "high" bipolar voltage, the unipolar slope and relative LAT stability of the signal may be calculated and analyzed. The unipolar slope, relative LAT stability, and TPI of the signal may be calculated and analyzed.

The algorithm may determine if it is a fractionated signal. The algorithm may also calculate the TPI for the signal. The algorithm may calculate the fractionation stability for the signal. Each one of these attributes may be an independent variable to the machine learning.

A plurality of second filters may be applied to the signals that passed the first filters. In some embodiments, the second filters that are applied to each signal is based on the characteristics of each signal. For example, the following filters may be applied to a signal determined to have LAT and high voltage to have one or more of the following characteristics: a unipolar slope of greater than or equal to 0.03 mV/ms and a relative LAT stability of 3 ms. The provided thresholds are by way of example only, and various other thresholds may be utilized in the algorithm. Further, a signal determined to have LAT and low voltage, in addition to having a unipolar slope greater than or equal to 0.03 mV/ms and a relative LAT stability of 3 ms, may also need a TPI which indicates that the signal was collected when the catheter 14 was in contact with tissue to pass the second filters.

The machine learning may learn that, for example, a signal determined to have no LAT and to not be fractionated may need a TPI which indicates that the signal was collected when the catheter was in contact with tissue to be considered a "good" point. A signal determined to have no LAT and to be fractionated, in addition to having a TPI indicating contact, may need a satisfactory fractionation stability to be considered a "good" point.

Signals that do not pass the second filters may be discarded. Signals that pass the second filters may be selected to be points in the point cloud to create an EP map of a target mapping site, such as a chamber of a heart.

According to an embodiment, neural network 1790 may be provided for selecting and detecting the best heartbeat at each spatial location as a cardiac mapping annotation and for improving the determination of cardiac mapping annotations. According to an exemplary embodiment, the neural network 1790 receives input data to train the neural network. The input data is preferably a set of attributes relating to a heartbeat. Non-limiting examples of the input data or attribute data can include:

- an ECG signal received from a mapping electrode around a reference annotation in an EP map;
- an ECG signal received by body surface electrode(s) around a reference annotation;
- an intracardiac EGM signal received by an electrode or by a bipolar electrode pair of a catheter, such as a mapping catheter, where the EMG signal can be a bipolar or unipolar EGM of an electrode of the mapping catheter around a reference annotation in an EP map;
- a spatial location of a mapping electrode at a reference annotation, which can be with or without respiration compensation;
- whether a heartbeat is incorporated into an EP map (e.g., heartbeat passes filters of heartbeat selector algorithm);
- a local annotation time of an acquired heartbeat, including any fix by a physician;
- a TPI of a mapping electrode at the time of a reference annotation;
- a force value, as detected by a force sensor of a mapping catheter, at the time of a reference annotation (typically measured in grams);
- a position of a reference annotation inside the respiration cycle when lung movements are monitored;
- a respiration gating status as a Boolean output;
- a difference between the current respiration cycle length minus previous cycle length;
- a ratio of current respiration cycle length divided by previous cycle length;
- a difference between the current respiration cycle length minus average or median cycle length;
- a ratio of current respiration cycle length divided by average or median cycle length;
- a distance of a mapping electrode at a current reference annotation from the spatial location of the same electrode at a previous reference annotation which can be measured by either actual locations or respiration compensated locations;
- an indication of whether there was any body surface activation at the time of this heartbeat (i.e., V interference);
- a discrete Boolean value (i.e., 0 or 1) as an input indicating whether a heartbeat has been deleted from the map by the physician; and
- any other EP data measured by an electrode of a catheter.

In an embodiment, one or more of the input data is fed into the neural network 1790. The input data can be stored in various locations, including, without limitation, a hospital or medical facility, at a remote server location, or in the cloud, without limitation. Training data can be manually or automatically transferred to a storage device associated with the neural network in real-time, at pre-determined intervals, upon request, when the mapping system 1720 is idle. As a result, the neural network 1790 can learn in real time or at predetermined times or intervals.

In an embodiment, an output of the neural network 1790 can include, without limitation:

a determination, such as a discrete Boolean value, indicating whether a current heartbeat has improved attributes over a prior heartbeat; and a determination of an accurate cardiac mapping annotation.

In the current state of the art, when an EA point in the cardiac EP mapping system is not good enough (for example, because the ECG in this EA point was noisy), the physician deletes this EA point and acquires a new EA point at approximately the same spatial location.

In accordance with an exemplary embodiment of the present application, a pair of deleted and re-acquired EA points obtained at approximately the same spatial location (i.e., same location, up to some tolerance) are used to train a machine learning algorithm. Given two EA points, the machine learning algorithm will learn that the re-acquired EA point has better characteristics than the deleted EA point. Once the machine learning algorithm is trained with enough data, given a pair of any two EA points, the algorithm may predict which one has better characteristics. The EP mapping system may use this information to automatically replace EA points with poor characteristics during the EP case. Before the mapping system would acquire a point in a spatial location and automatically use that one in the mapping and disregard any other points acquired in that location. In this system, multiple points may be acquired and the system can determine which ones should be used in the mapping system. The inputs of the machine learning algorithm preferably include one or more of the foregoing input data.

According to an exemplary embodiment, the neural network 1790 can comprise a convolutional neural network (CNN) or a recurrent neural network (RNN) such as a long short-term memory (LSTM) neural network. A CNN is a deep learning algorithm preferably used in the field of computer vision and/or image recognition. A CNN assigns importance (learnable weights) to various aspects or feature in an input image in order to differentiate one from the other. An LSTM neural network is a RNN having feedback connections used for deep learning.

In an embodiment, the EP mapping system vendor may ship systems with a pre-trained network. Hospitals can preferably continue to train the system. In an embodiment, a single model may be maintained for all hospitals, or for a group of hospitals, or every hospital may maintain its own model.

In an exemplary embodiment, after each training, the training model, including its output, can be executed against a standard database, such as a gold standard database, to validate its accuracy. In an exemplary embodiment, if the accuracy of the newly trained model is below a threshold, or alternatively, if the accuracy of the newly trained model is less than the accuracy of a previous model, the model can be discarded. Similarly, if the accuracy of the newly trained model is at or above a threshold, or alternatively, if the accuracy of the newly trained model is greater than the accuracy of a previous model, the model may be published to the EP mapping systems in the field. In an exemplary embodiment, the publication of the new model can be performed manually, for example, by an operator downloading a file from a web address and uploading it to the mapping system 1720. Alternatively, the new model can be pushed to the mapping system 1720 in the field via the Internet.

In EP mapping, with an intra-body probe, typically a catheter with multiple mapping electrodes disposed along the body of the catheter near the catheter distal end, is inserted into a cavity of the heart. Time varying ECG signals are recorded at multiple contact points between the mapping electrodes and the heart tissue. The multiple ECG electrodes are then moved to different contact positions within the heart tissue and the process is repeated. Then, metrics regarding cardiac function are computed from the local ECG signals, which are mapped spatially across the surface of the heart cavity. The mapping assists the medical professional to identify regions of heart dysfunction.

Electrical sources in the heart, such as the sinoatrial (SA) and atrioventricular (AV) nodes initiate electrical activity waves that propagate over the heart triggering the muscle tissue in the atria and ventricles to contract in a characteristic sinus rhythm. When the activity wave-front reaches the multiple mapping electrodes during each cardiac cycle, the characteristic ECG waveforms are detected at the multiple mapping electrodes. These waveforms are time-shifted due to the different arrival times of the same wave-front at the different multiple electrodes contacting the tissue at different spatial locations along the surface of the heart cavity.

The arrival times of the ECG waveforms detected at the multiple mapping electrodes can be used to map the propagation time and/or velocity of the activity wave across the heart. The mapping of the activity wave is performed with respect to a single time reference indicative of the cardiac cycle, referred to as the reference annotation time.

The reference annotation time can be computed by processing the ECG signals obtained from a body surface electrode, or from an IC reference electrode on an additional catheter and placed in contact with the surface of the cardiac chamber. Typically, the physician designates whether the reference annotation time is computed from a BS or IC channel, depending on the suspected pathology. However, if during the course of the mapping procedure the assigned ECG reference channel fails (e.g., due to poor reference electrode contact, system noise, or other impairments), remapping needs to be performed. Remapping of the heart is time consuming and uncomfortable for the patient.

Figure 20:
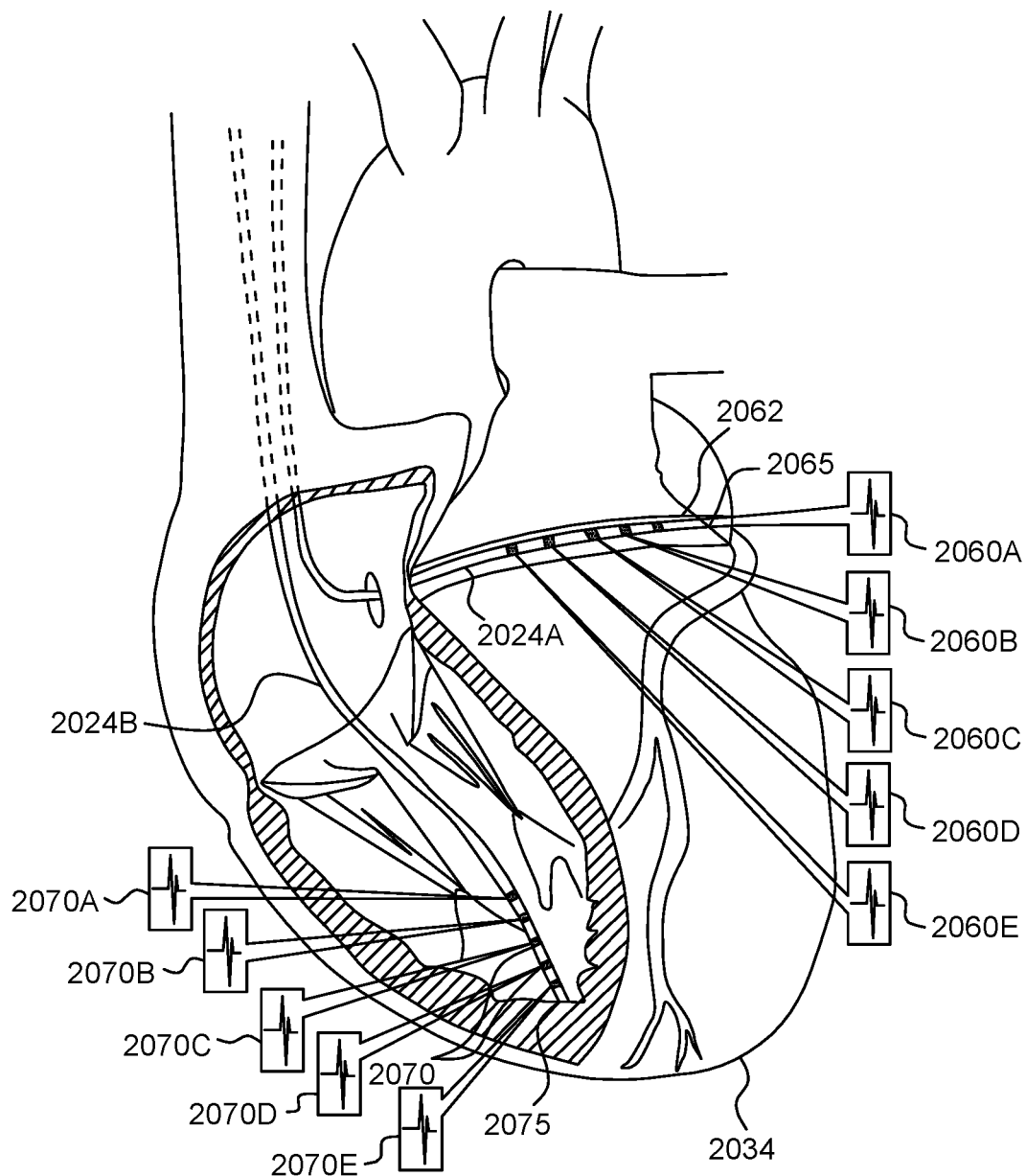
FIG. 20 is an exemplary illustration of a plurality of electrodes sampling multiple contact points in a heart cavity, in accordance with an exemplary embodiment of the present application.

FIG. 20 is an exemplary illustration of a plurality of electrodes sampling multiple contact points in a heart cavity, in accordance with an embodiment of the present application. In the exemplary embodiment shown in FIG. 20, IC catheter 2024A is inserted into a coronary sinus 2062 of heart 2034. The catheter preferably comprises five reference ECG electrodes 2060A-2060E disposed at points along the length of the body of catheter 2024A near a distal end 2065. Reference ECG electrodes 2060A-2060E contact multiple tissue points on the surface of the coronary sinus and are used to measure respective reference ECG signals at the multiple contact points.

Similarly, IC catheter 2024B is inserted into the right ventricle of heart 2034. The catheter comprises five mapping electrodes 2070A-2070E at points along the body of catheter 2024B near a distal end 2075. Mapping electrodes 2070A-2070E contact multiple tissue points on the surface of the right ventricle and are used to measure respective mapping ECG signals at the multiple contact points.

The five reference ECG electrodes 2060A-2060E and multiple mapping electrodes 2070A-2070E shown in FIG. 20 are depicted merely for conceptual clarity and not by way of limitation of the present claims. In alternative embodiments, any suitable number of mapping and reference electrode configurations can be used. For example, instead of a single electrode for unipolar ECG detection, the electrodes can be arranged in pairs for bipolar ECG detection. Any suitable number of mapping and reference catheters can be used in any suitable configuration. Reference catheter 2024A and mapping catheter 2024B, or any number of catheters, could be navigated into a suitable location within heart 2034 to perform the functions described herein.

An ECG signal interface, such as processor 1741 (shown in FIG. 17), receives and processes signals from body surface electrodes, such as body surface electrodes 1743 (shown in FIG. 17), IC ECG reference electrodes 2060A-2060E and mapping electrodes 2070A-2070E. Cardiac mapping is performed by moving multiple mapping electrodes 2070A-2070E across the surface of the cardiac tissue and recording the ECG at each contact point along with the location of the electrode when the ECG waveform was recorded. Alternatively, cardiac mapping may comprise inserting reference and/or mapping electrodes externally into the patient's body, for example through the chest cavity, to contact the surface of the cardiac tissue.

The data recorded at each mapping point is also referred to as a mapping annotation. However, since the activation wave front propagates to the different electrodes at spatially different points on the endocardium, the local ECG signals arrive at different points, and thus to different electrodes, at different times. The difference in the arrival time of the ECG signal to a given ECG electrode is an indication of the local activation wave front velocity. The difference between the measured time of the ECG signal arriving at a particular mapping electrode for a particular cardiac cycle, or heartbeat, relative to a single timing reference indicative of cardiac cycle timing of the heart is known herein as the LAT. Similarly, the single timing reference is referred to as the reference annotation time.

A typical cardiac map comprises a mapping of the LATs on multiple different points on the heart surface, a propagation map showing the activation wave front at different times across the heart, and characteristic voltages of the ECG at the same given points. A user, such as a physician, can then use changes from the expected activity wave front and/or voltages shown in the cardiac map to detect regions of heart dysfunction, such as atrial or ventricular tachycardia. Ablation therapy, for example, may be used to correct the dysfunction.

In some embodiments, processor 1741 uses acquired reference ECG signals in computing the reference annotation time from BS electrodes 1743 and/or from IC reference electrodes 2060A-2060E. Acquired IC mapping ECG signals are acquired as the mapping electrodes are moved across the cardiac tissue and the ECG recorded for acquiring the mapping data points. However, the multiple IC reference electrodes contact the cardiac tissue and are not moved during the medical procedure. Depending on the type of anticipated pathology, the physician typically designates whether the reference annotation time is be computed from ECG taken from BS electrodes 1743 or from IC reference electrodes 2060A-2060E.

Example 1

In an exemplary embodiment, a machine learning algorithm, such as a neural network, can utilize attributes of two heartbeats as inputs, learn to identify which heartbeat exhibits better characteristics based on predetermined criteria, and output a binary result, as described in more detail below with respect to FIGS. 18 and 19. Exemplary attributes for identifying which heartbeat is better includes, without limitation, the heartbeat with less noise, with a more obvious LAT activation, with a more obvious late potential, with a more stable fractionation, with less V interference etc. In an embodiment, the heartbeats are obtained from stable arrhythmias.

Conventional EP mapping systems either acquire the first heartbeat at every spatial location or use rule based systems to select the best heartbeat at every spatial location. For example, when a physician acquires a first heartbeat at a specific spatial location, subsequent heartbeats are prevented from being acquired, even if the first heartbeat displayed poor characteristics. The system and method disclosed in this example collects a plurality of heartbeats at a specific spatial location and learns to select the best heartbeat at each spatial location via machine learning.

Figure 18:
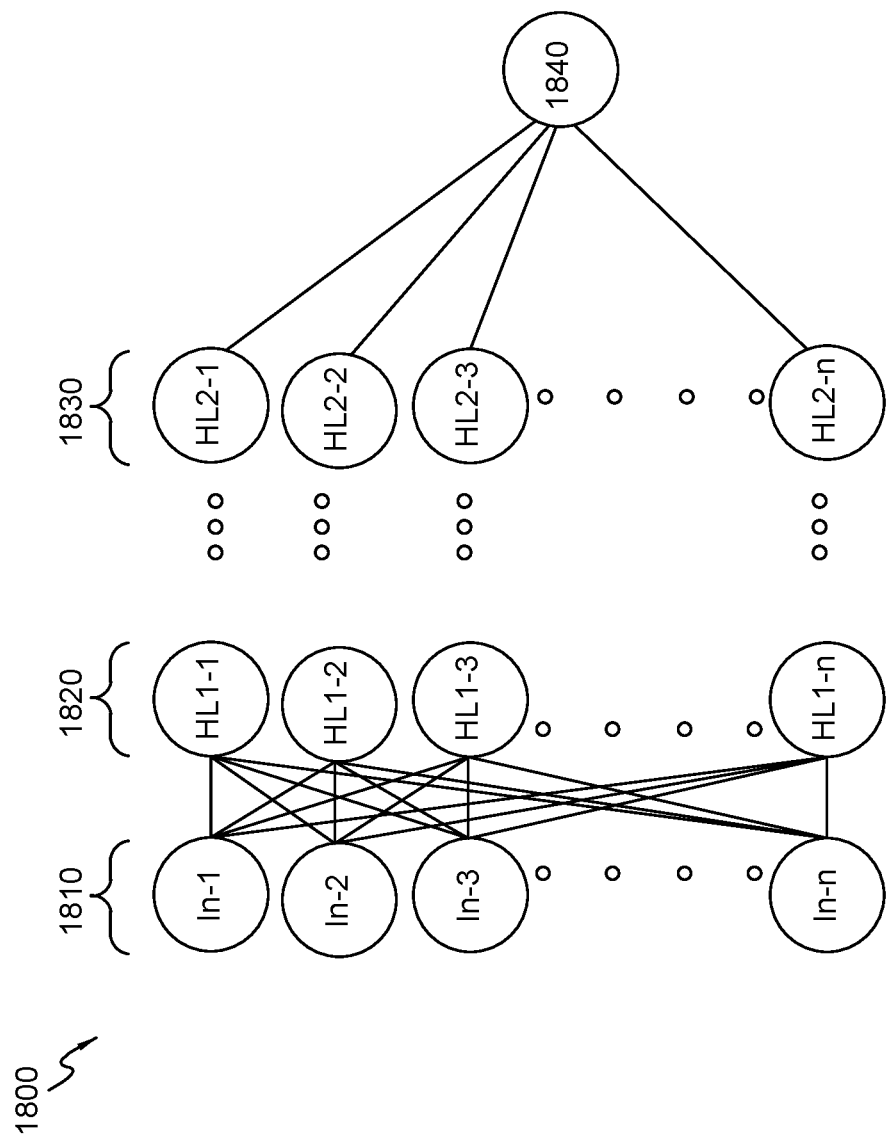
FIG. 18 illustrates an exemplary embodiment of a convolutional neural network that can receive the attributes of two heartbeats and learn to identify which heartbeat is better in accordance with the present application.

FIG. 18 is an exemplary embodiment of a CNN 1800 that can receive the attributes of two heartbeats and learn to identify which heartbeat is better in accordance with the present application.

Referring to FIG. 18, in an exemplary embodiment, neural network 1800 is a CNN. The CNN 1800 preferably receives input data 1810. In an embodiment, the input data 1810 preferably include a first set of input data relating to attributes of a first heartbeat and a second set of input data relating to a second heartbeat obtained at the same spatial location as the first heartbeat. The first and second set of input data can comprise inputs In-1, In-2, In-3, . . . , In-n, wherein "n" is the last of the plurality of inputs. For example, the first set of input data can comprise inputs In-1 and In-2, and the second set of input data can comprise In-3 and In-n. The first and second set of input data can be input into the CNN during the same cycle or during separate cycles. The input data 1810 can comprise attributes of heartbeats, which preferably include, without limitation:

an intracardiac EGM signal received by an electrode or by a bipolar electrode pair of a catheter, such as a mapping catheter, where the EMG signal can be a bipolar or unipolar EGM of an electrode of the mapping catheter around a reference annotation in an EP map;

an ECG signal received from a mapping electrode around a reference annotation;

ECG signal received by body surface electrode(s) around a reference annotation;

a TPI of a mapping electrode at the time of the reference annotation;

a force value, as detected by a force sensor of the mapping catheter, at the time of the reference annotation (typically measured in grams);

a spatial location or distance vector of a mapping electrode at a reference annotation, which can be with or without respiration compensation;

a respiration status vector around the reference annotation;

a position of the reference annotation inside the respiration cycle when lung movements are monitored;

a difference between the current respiration cycle length minus previous cycle length;

a ratio of current respiration cycle length divided by previous cycle length;

a difference between the current respiration cycle length minus average or median cycle length;

a ratio of current respiration cycle length divided by average or median cycle length;

an indication of whether a physician manually accepted the heartbeat into the EP mapping system or deleted the heartbeat; and a distance of the mapping electrode at the current reference annotation from the spatial location of the same electrode at the previous reference annotation which can be measured by either actual locations or respiration compensated locations. In other words, the distance the electrode moved since the last heartbeat, for example, according to either actual locations or respiration-compensated locations, as an indication of the stability of the catheter.

The input data 1810 is provided to a first hidden layer 1820 including nodes HL1-1, HL1-2, HL1-3, . . . HL1-n, and optionally, to a second or more hidden layers 1830 including nodes HL2-1, HL2-2, HL2-3, . . . HL2-n, which are combined to produce an output 1840. The hidden layers 1820, 1830 utilize data from the input to determine which of the first or second heartbeats has better characteristics, such as, without limitation, the heartbeat with less noise, a more obvious LAT activation, a more obvious late potential, a more stable fractionation, less V interference, etc. Over time, the neural network learns the weights to apply to the input data.

In some embodiments, the output 1840 is a value indicating, for example, whether the first or second heartbeat in a pair of heartbeats taken at the same spatial location is better. For example, in CNN 1800, all inputs 1810 are fed to the neural network at once to calculate the output 1840.

Figure 19:
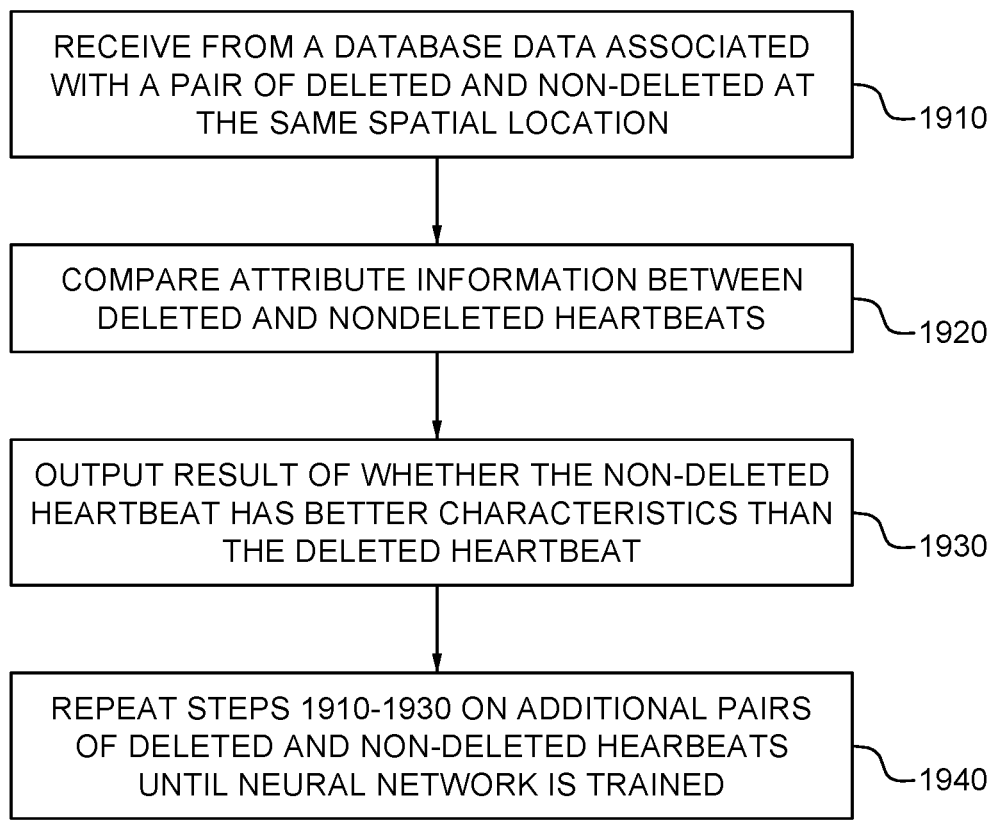
FIG. 19 is an exemplary flow diagram depicting a method for training a neural network to obtain attributes of two heartbeats and learn to identify which heartbeat is better in accordance with the subject matter of the present application.

FIG. 19 is an exemplary flow diagram depicting a method for training a neural network 1900 to obtain attributes of two heartbeats and learn to identify which heartbeat is better in accordance with the present application.

At 1910, the CNN 1800 preferably receives from a database a pair of deleted and non-deleted heartbeats obtained at the same spatial location. The received data is input data 1810 for the CNN 1800 and preferably includes sets of attribute data corresponding to each heartbeat in the heartbeat pairs obtained at the same spatial location. For example, the sets of attribute data can be any of the input data 1810 described above for each heartbeat.

At 1920, the hidden layers 1820, 1830 of the CNN 1800 preferably compare the sets of attribute information between the deleted and non-deleted heartbeats to determine which of the first or second heartbeats has better characteristics based on predetermined criteria, such as, without limitation, the heartbeat with less noise, a more obvious LAT activation, a more obvious late potential, a more stable fractionation, less V interference, manual physician deletion, etc. For example, if the first heartbeat was manually deleted by a physician, and a second heartbeat was manually acquired by a physician, the CNN 1800 considers the second heartbeat to have better characteristics than the first heartbeat. The CNN 1800 compares the attribute information associated with each heartbeat to learn optimal heartbeat characteristics.

At 1930, the CNN 1800 outputs a result indicating whether the non-deleted heartbeat has better characteristics than the deleted heartbeat.

At 1940, the CNN 1800 preferably repeats 1910, 1920, and 1930 on additional pair of deleted and non-deleted heartbeats obtained at the same spatial location until the CNN 1800 is trained.

In an embodiment, once the CNN 1800 is trained, it can be used to replace sub-optimal heartbeats in an EP mapping system with heartbeats at the same spatial location having better characteristics in real-time or following a procedure. For example, the EP mapping system will initially acquire a first heartbeat at the spatial location X, Y, Z. When another heartbeat is recorded at the same spatial location, the system will execute the CNN using the attribute data of each heartbeat as input data, and output a determination as to which heartbeat has better characteristics. If the first heartbeat is determined to be better, the second heartbeat is discarded from the EP mapping system. If the second heartbeat is determined to be better, than the first heartbeat will be automatically replaced by the second heartbeat in the EP mapping system.

The training model described above is preferably supervised by a physician, on-site at a hospital, at a remote training facility.

An advantage of utilizing CNN 1800 to receive the attribute data of two heartbeats and learn to identify which heartbeat is better in accordance with the present application is that the CNN 1800 can learn to mimic the decisions of a physician by looking at the heartbeats that are deleted by the physician. In addition, by determining the best heartbeat at a spatial location, a physician can more accurately determine characteristics of the heartbeat, such as LAT value, peak-to-peak bipolar voltage value, an ECG signal, and an EGM signal.

In the embodiments described above, the machine learning took two heartbeats and determined which one was better. The system was trained with pair of heartbeats (one deleted and one re-acquired heartbeat at approximately the same spatial location in the heart). Now, we describe another embodiment for the same purpose. In this embodiment, each heartbeat is assigned a grade. For example, in an embodiment the first heartbeat and the second heartbeat may each be assigned a grade of 0, 0.5 or 1. If a physician deletes a heartbeat, the heartbeat receives a grade of 0; if a physician acquires a new heartbeat at the approximately same location, the heartbeat receives a grade of 1; and all other heartbeats receive a grade of 0.5. Unlike the previously described embodiments that took two heartbeats and predicted which one is better, this embodiment takes a set of attributes for a single heartbeat and predicts a grade for the single heartbeat. If the heartbeat has the characteristics of the heartbeats that the physician generally deletes, the machine learning will likely output a number around 0. If the heartbeat has the characteristics of the heartbeats the physician generally re-acquires after deleting a bad one, the machine learning will likely output a number around 1. In this embodiment, grade is a continuous variable (not a discrete category). Although we train the machine learning with grades of 0, 0.5 and 1 only, the machine learning can output any real number. In this embodiment, during the runtime (in other words, during the inference phase, while the physician performs the electrophysiological study of the patient), when the system needs to understand which heartbeat is better, it can predict the grade of each heartbeat independently, and the heartbeat with the highest grade can be considered as the best heartbeat.

Example 2

In an exemplary embodiment, a machine learning algorithm, such as a neural network, can receive EP data representing multiple heartbeats obtained at the same spatial location and learn to select and output the best mapping annotation for an EP mapping system based on any of the inputs described above.

Figure 22:
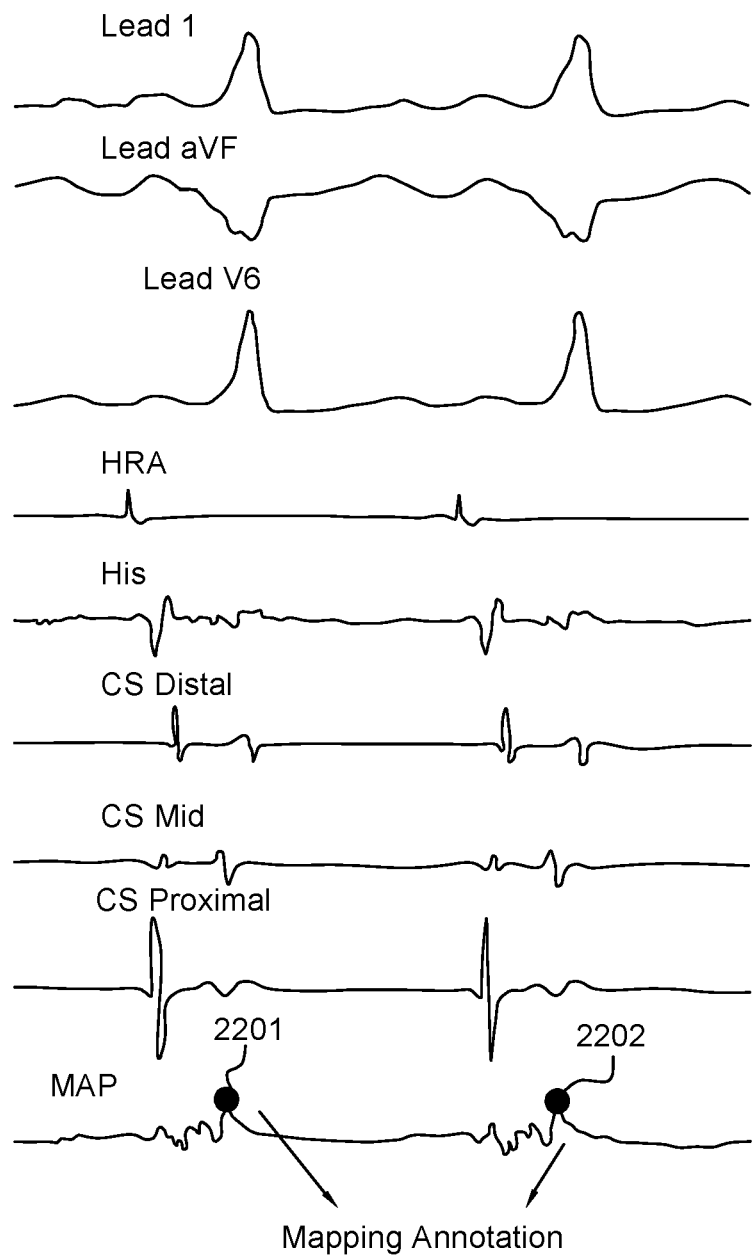
FIG. 22 is an exemplary illustration of fixing a mapping annotation based on the highest peak voltage of the ECG signal around a reference annotation in accordance with the subject matter of the present application.

In traditional rule based EP mapping systems, the mapping annotation is typically determined based on the highest peak voltage 2201 of the ECG signal around the reference annotation, or the highest negative derivative 2202 of the ECG signal around the reference annotation as depicted in FIG. 22. A physician may accept the mapping annotation or may move the mapping annotation if the result is not satisfactory. Examples of reasons why a physician may move the mapping annotation include, for example and without limitation, the heartbeat has significant noise, a less obvious LAT, a less obvious late potential, a less stable fractionation, more V interference, etc.

In accordance with the subject matter of this application, a neural network can receive attributes of multiple heartbeats at the same spatial location and learn to identify the best mapping annotation based on the input data described above. In an embodiment, the heartbeats are obtained from stable arrhythmias.

In an embodiment of the subject matter of the present application, at the beginning, the neural network or machine learning system is trained to find the same mapping annotation calculated by a rule-based system. The rule-based system uses a plurality of rules to choose an action. The plurality of rules may be defined by a human programmer. In some embodiments, the plurality of rules is in the form of if-then statements. For example, initially, many ECG signals and a corresponding mapping annotation calculated by the rule-based system for each ECG signal will be fed to the machine learning system to train it. This is expected to make the machine learning system almost as accurate as the rule-based system. As physicians at various locations start using this system, the initial results will be similar to the rule-based system. However, every time a physician fixes the mapping annotation manually, this information is used to train the machine learning system, which is preferably a self-learning system. In an embodiment, a single model may be maintained for all hospitals, or each hospital or hospital group can maintain its own model. After the machine learning system is trained, the performance of the model may be validated against a gold standard to validate that its accuracy is above a predetermined threshold and/or better than the accuracy of the previous model. Over time, the machine learning system will make the machine learning algorithm better than the rule-based system.

Figure 21:
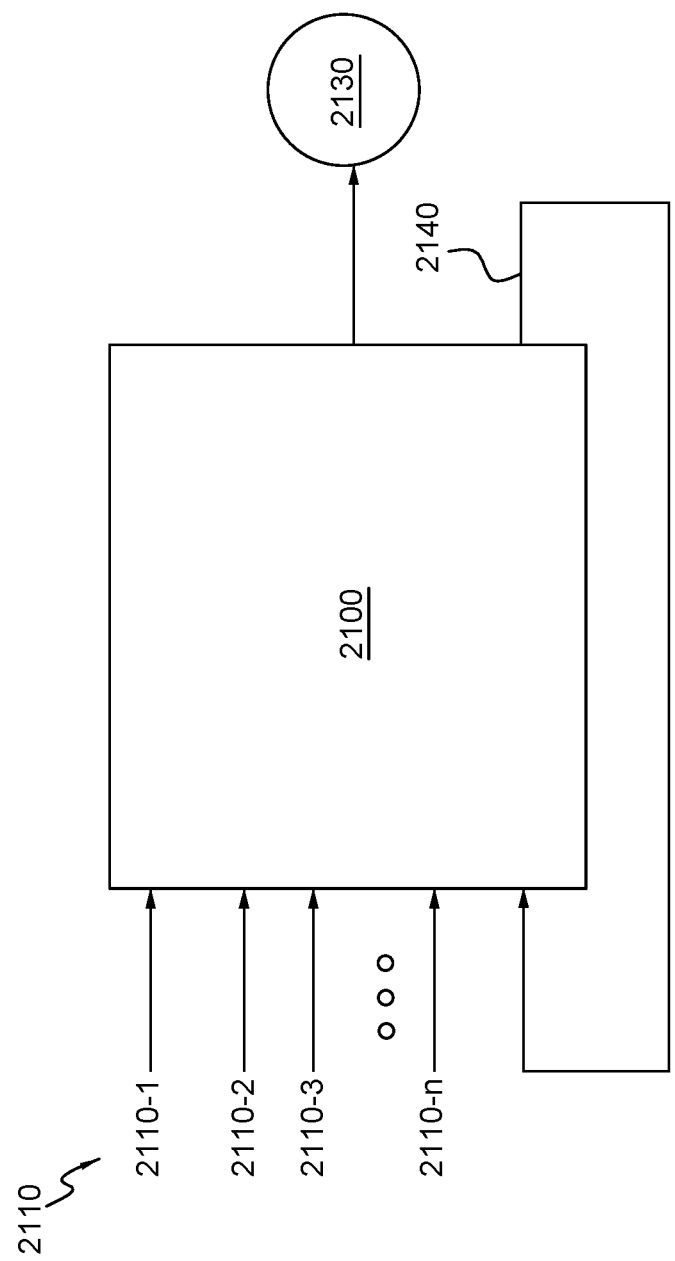
FIG. 21 illustrates an exemplary embodiment of a recurrent neural network can receive attributes of multiple heartbeats at the same spatial location and learn to identify the best mapping annotation in accordance with the subject matter of the present application.

Referring to FIG. 21, in an exemplary embodiment, the neural network is a RNN 2100. The RNN 2100 preferably receives input data 2110. In an embodiment, the input data 2110 can comprise attribute data for each of a plurality of heartbeats 2110-1, 2110-2, 2110-3, . . . 2110-n obtained from the same spatial location. For example, the attribute data can be derived from one of mapping electrodes 2070A-2070E depicted in FIG. 20. The attribute data for each heartbeat can comprise any of the attributes described herein. Each cycle of the RNN receives all attribute data relating to each heartbeat as opposed to providing attribute data for a single heartbeat. In addition, as shown with reference to arrow 2140 in FIG. 21, if the accuracy of the newly trained model is at or above a threshold, or alternatively, if the accuracy of the newly trained model is greater than the accuracy of a previous model, the model can be used as an input for the neural network.

The inputs 2110 are provided to the RNN 2100, and are combined to produce an output 2130, such as an identification of the best mapping annotation. As more heartbeat samples are fed to the RNN 2100, the output 2130 becomes more accurate.

In an embodiment, to train a model, a physician's acceptance of a heartbeat as a mapping annotation may be an input for the RNN 2100, along with other heartbeats obtained from the spatial location. It is expected that the physician accepted heartbeat will have better characteristics than the other heartbeats obtained at the same spatial location, and the RNN 2100 will output the physician accepted heartbeat as the best mapping annotation. The RNN 2100 compares the attribute information associated with each heartbeat with the physician accepted heartbeat to learn optimal heartbeat characteristics. Over time, the RNN 2100 learns the characteristics of the attributes of the physician accepted heartbeat to train the model.

The output of the RNN, such as output 2130, can be used to train the RNN 2100. For example, as shown with reference to arrow 2140 in FIG. 21, if the accuracy of the output 2130 is at or above a threshold, the output 2130 can be used as an input 2110 for the neural network 2100.

In addition, for example, as discussed above, after each training, the training model, including its output, can be executed against a standard database, such as a gold standard database, to validate its accuracy. In an exemplary embodiment, if the accuracy of the newly trained model is below a threshold, or alternatively, if the accuracy of the newly trained model is less than the accuracy of a previous model, the model can be discarded. Similarly, if the accuracy of the newly trained model is at or above a threshold, or alternatively, if the accuracy of the newly trained model is greater than the accuracy of a previous model, the model may be published to the EP mapping systems in the field.

In an embodiment, once the RNN 2100 is trained, it can be used to improve mapping annotations in an EP mapping system in real-time or following a procedure.

In an embodiment, training of the RNN 2100 can be supervised at the facility where the cardiac procedure is taking place, such as a hospital or medical facility, or at a remote location, such as a training center.

Example 3

In an exemplary embodiment, a machine learning algorithm, such as a neural network, can receive data representing a heartbeat and any manual correction of the mapping annotation, such as a correction performed by a physician, and learns to calculate a mapping annotation for an EP mapping system.

In traditional mapping annotation systems, such as rule based systems, the mapping annotation is determined based on intracardiac ECG activation. ECG activation is conventionally determined in a number of ways such as, without limitation, the onset of the bipolar EGM, the time of the maximum bipolar amplitude, or by combining various features of the ECG signal such as, for example and without limitation, the manner described in US Patent Publication No. 2018/00042504. A physician needs to review the determined mapping annotation for accuracy. If the mapping annotation in not accurate, the physician must manually move the mapping annotation to fix it.

Figure 23:
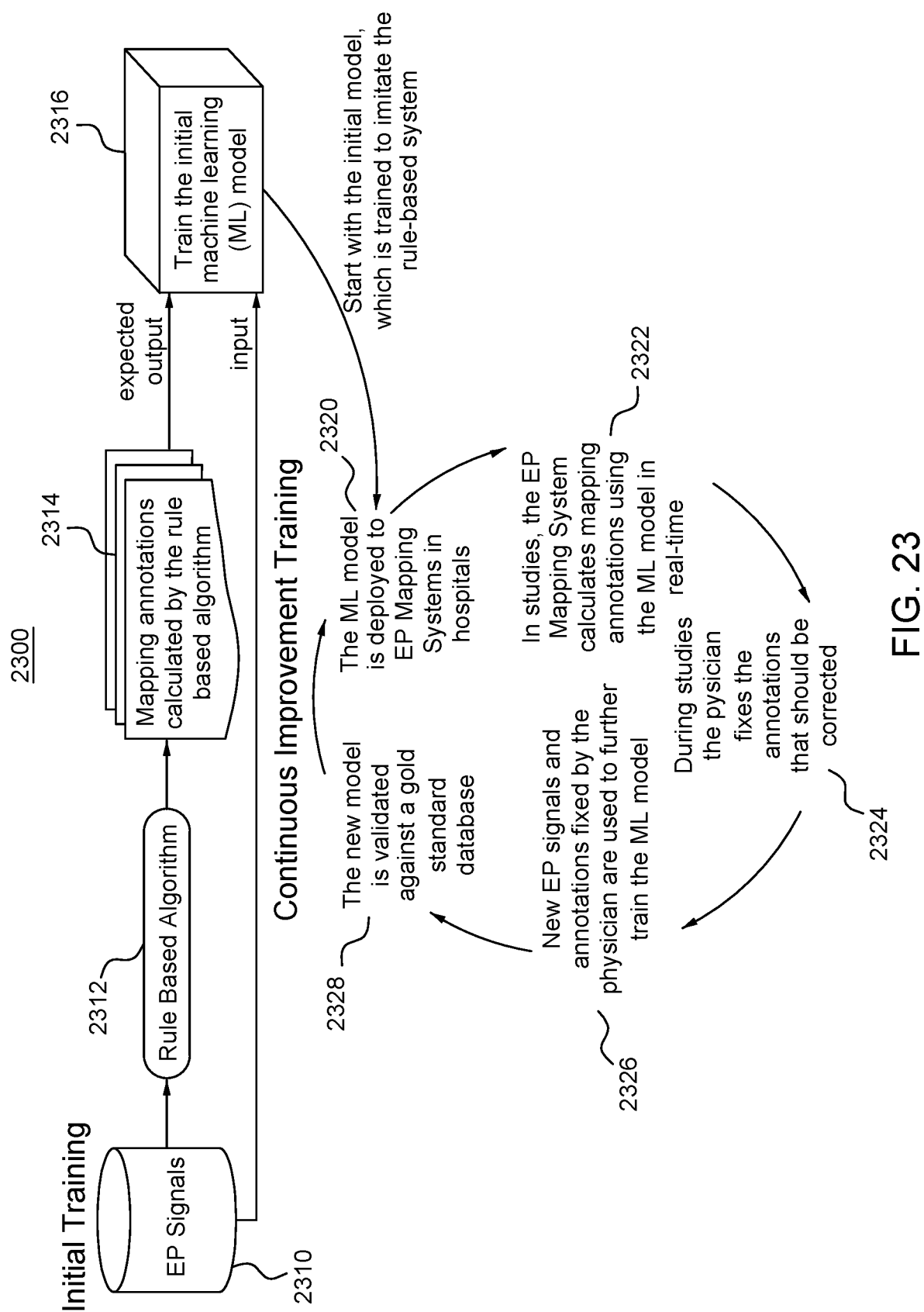
FIG. 23 is an exemplary flow diagram depicting a system and method for training a machine learning algorithm to determine a mapping annotation in accordance with subject matter of the present application.

FIG. 23 is an exemplary flow diagram depicting a method for training a machine learning system, such as a neural network, to calculate mapping annotations in intracardiac signals, such as EGM signals, in accordance with the present application. In an embodiment, the neural network can be any kind of neural network, such as a CNN or RNN, similar to those described with reference to FIGS. 18 and 21.

2310-2316 of FIG. 23 depict a preferred system and method for training an initial model for a machine learning system in accordance with an embodiment. At 2310, the machine learning system preferably receives input data relating to an EP signal. For example, the input data can comprise, without limitation, one or more of the following:
  a bipolar EGM signal of a mapping catheter around a reference annotation;
  a unipolar EGM signal of a mapping catheter around a reference annotation;
  an ECG signal received by body surface electrode(s) around a reference annotation;

a start of a window of interest (WOI);
an end of a WOI;
a spatial location, such as 3D coordinates, of a mapping electrode around a reference annotation;
a TPI of a mapping electrode around the reference annotation;
a force value, as detected by a force sensor of the mapping catheter, at the time of the reference annotation (typically measured in grams);
a respiration status vector around the reference annotation;
a position of the reference annotation inside the respiration cycle when lung movements are monitored;
a difference between the current respiration cycle length minus previous cycle length;
a ratio of current respiration cycle length divided by previous cycle length;
a difference between the current respiration cycle length minus average or median cycle length;
a ratio of current respiration cycle length divided by average or median cycle length;
an indication of whether a physician manually accepted the heartbeat into the EP mapping system or deleted the heartbeat; and
a distance of the mapping electrode at the current reference annotation from the spatial location of the same electrode at the previous reference annotation which can be measured by either actual locations or respiration compensated locations. In other words, the distance the electrode moved since the last heartbeat, for example, according to either actual locations or respiration-compensated locations, as an indication of the stability of the catheter.

At 2312 a rule-based algorithm is preferably applied to the input data, and at 2314 a mapping annotation is calculated by the rule-based algorithm. At 2316, the mapping annotation is output as an initial model to train further the machine learning system. The initial model is preferably trained to imitate the rule-based algorithm.

In some embodiments, a signal may be shifted in order to obtain shifted signals. The sifted signals may be used as additional input data at 2310. For example, if data corresponding to a bipolar and two unipolar signals is being used as the input data, the signal may be shifted 1 ms to the left, 2 ms to the left, 3 ms to the left, 4 ms to the left, 5 ms to the left, 6 ms to the left, 7 ms to the left, 8 ms to the left, 9 ms to the left, 10 ms to the left, 1 ms to the right, 2 ms to the right, 3 ms to the right, 4 ms to the right, 5 ms to the right, 6 ms to the right, 7 ms to the right, 8 ms to the right, 9 ms to the right, and 10 ms to the right. As such, in this example, 21 different signals may be obtained. When the shifted signals are fed to the neural network, the neural network may learn that the signals are time invariant. This may allow for the training to be done with less input data.

In some embodiments, signals may be augmented by adding low-frequency noise and/or high-frequency noise. The low-frequency noise may represent the effect of respiration and high-frequency noise may represent electromagnetic noise. For example, the following four signals may be obtained from a single signal: the signal itself, the signal with an added 1 Hz of noise, the signal with an added 450 Hz noise, the signal with an added noise of 1 Hz and 450 Hz. In this way, the convolutional layer of the CNN may learn to ignore low-frequency noise and high-frequency noise more quickly and efficiently.

In some embodiments, a combination of time shifting and noise adding may be used. For example, a signal may be shifted 1 ms to the left with 1 Hz of noise added, shifted 2 ms to the left with 1 Hz of noise added, etc.

2320-2328 of FIG. 23 depict an embodiment of continuous improvement training of a deployed model for a machine learning system in accordance with an embodiment. At 2320, the deployed model is deployed to an EP mapping system in an environment, such as a hospital or medical testing facility. In an embodiment, the deployed model can be the initial model or a new model.

In some embodiments, the deployed model may be downloaded from a central server. The data downloaded from the central server may be signed with a private key, where the private key is known by the central server only. The public key that corresponds to the aforementioned private key may be known by a medical device downloading the deployed model from the central server. In some embodiments, a public/private key mechanism in HTTPS or a similar protocol, such as SFTP, may also be used to ensure the security of the download. In these embodiments, the medical device may check the URL address of the central server and validity of the Secure Sockets Layer (SSL) certificate.

At 2322, the EP mapping system uses the deployed model to calculate mapping annotations in real-time. For example, and without limitation, when the deployed model is the initial model, the rule-based algorithm is used to calculate the mapping annotation utilizing the rule-based algorithm.

Figure 24:
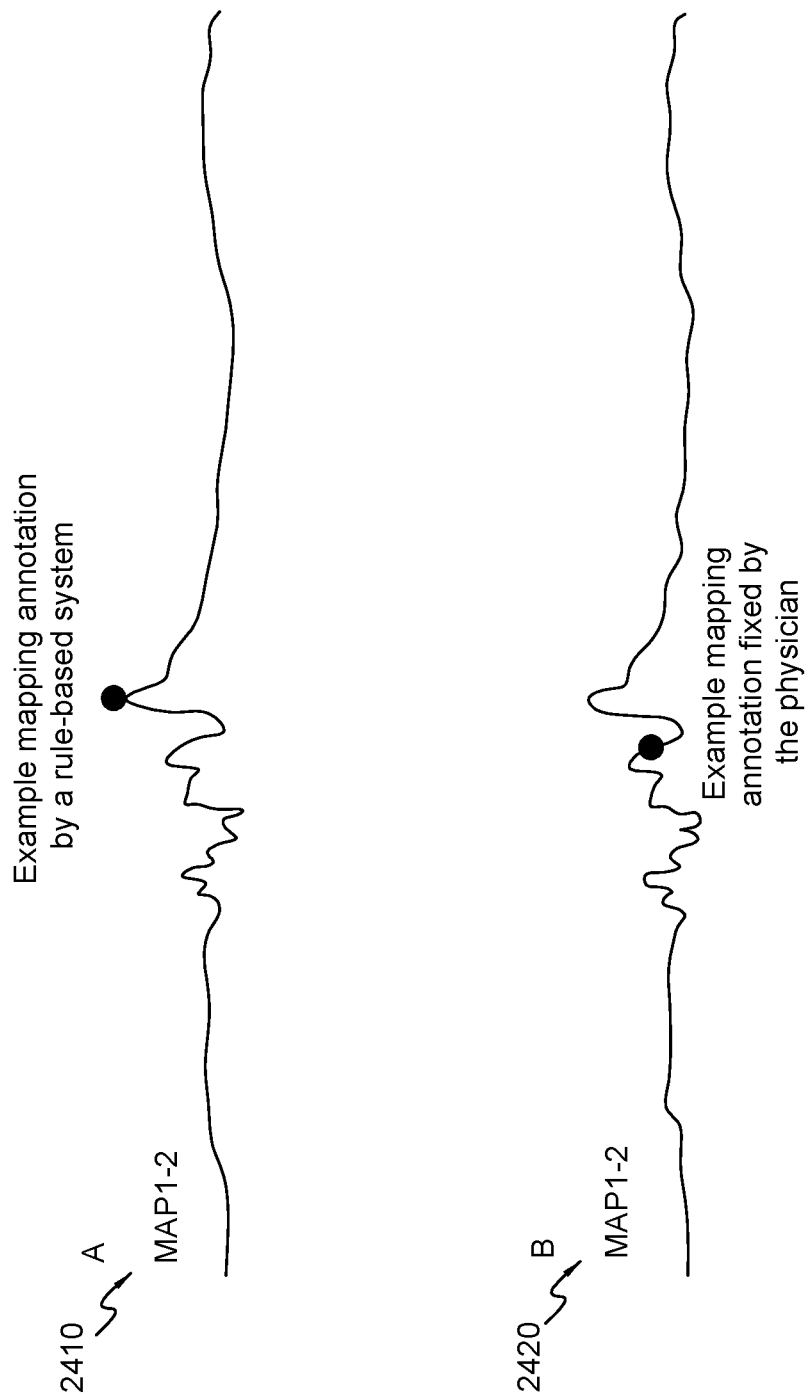
FIG. 24 is an exemplary illustration of an EGM signal showing a mapping annotation fixed by a rule based system and an EGM signal showing a mapping annotation manually fixed by a physician.

At 2324, a physician can manually fix the mapping annotation in the EP mapping system if the mapping annotation is not accurate. The machine learning system preferably receives data relating to the mapping annotation manually fixed by a physician in the EP mapping system. The corrections of the physician may be fed to the machine learning system in real time, over the cloud, or via an off-line device, such as memory stick, CD, digital versatile disks (DVD), etc. In an embodiment, the corrections of the physician may be manually checked before they are fed to the machine learning system. EGM signal A 2410 in FIG. 24 illustrates an example of a mapping annotation fixed by a rule-based system. EGM signal B 2420 in FIG. 24 illustrates an example of a mapping annotation manually fixed by a physician.

In some embodiments, the corrections of the physician may be signed by the medical device before they fed to the machine learning system. The machine learning system may check the corrections of the physician to ensure they indeed came from the medical device. In some embodiments, a private/public key may be used. For example, the private key may be known by the medical device and the public key may be known by the machine learning system. In further embodiments, the private key may be held in a temper-resistant hardware security module on the medical device. Additionally, or alternatively, the private key of the medical device may be stored inside a trusted platform module embedded to the mainboard of the medical device. In further embodiments, the private/public key method may be combined with an IP whitelisting (e.g., private key P1 shall come from the IP address xxx.x.xxx.x). In some embodiments, a plurality of medical devices contain the same private key. In other embodiments, a different private key can be deployed to each medical device. In some embodiments, to enhance security, the user may be asked to provide a user name and a password while uploading the data. The username and password may be combined with the private key method and/or IP whitelisting.

At 2326, the machine learning system preferably further trains the deployed model by using new EP signals and the mapping annotation manually fixed by the physician in the EP mapping system.

At 2326, the machine learning system preferably further trains the deployed model by using new EP signals and the mapping annotation(s) fixed by the physician. As discussed above, initially, the machine learning system will calculate the mapping annotations based on the results of rule-based algorithms. However, as the neural network received more mapping annotations manually fixed by physicians, the machine learning system will learn from the corrections made by the physicians and more accurately calculate the mapping annotations.

At 2328, the machine learning system preferably outputs a new model. In an embodiment the output can further include at least one of a mapping annotation and a Boolean value indicating whether the mapping annotation can be calculated or not. For example, the machine learning system may learn that under some conditions, such as insufficient force, when the catheter is not stable, etc., the mapping annotation cannot be calculated. The Boolean output may be implemented as a neuron that outputs a real number. Optionally, a logit function may be applied to the output number in which the Boolean value will be assumed to be true when the number is above a predetermined threshold value and considered incorrect when the number is below a predetermined threshold value. In an embodiment, a user can set the predetermined threshold, for example, by operating a slider bar in a graphical user interface.

At 2328, the new model, including its output, can optionally be executed against a standard database, such as a gold standard database, to validate its accuracy. In an exemplary embodiment, if the accuracy of the newly trained model is below a threshold, or alternatively, if the accuracy of the newly trained model is less than the accuracy of a previous model, the model can be discarded. Similarly, if the accuracy of the newly trained model is at or above a threshold, or alternatively, if the accuracy of the newly trained model is greater than the accuracy of a previous model, the model may be published to the EP mapping systems in the field. Once the new model is validated, it can be deployed to the EP mapping system at 2320.

If the accuracy of the newly trained model is worse than the accuracy of a previous model, but above a threshold, the results of the newly trained model may be sent to a human expert. The human expert may compare the expected results of the gold standard database to the results calculated by the newly trained mode. If the human expert believes the results of the newly trained model is better than the gold standard, the human expert may mark the results of the newly trained model as the expected results, to that the gold standard database may be updated.

In an embodiment, once the machine learning system is trained, it can be used to improve mapping annotations in an EP mapping system in real-time or following a procedure.

In an embodiment, training of the machine learning system can be supervised at the facility where the cardiac procedure is taking place, such as a hospital or medical facility, or at a remote location, such as in the cloud or at a training center.

Although features and elements are described above in particular combinations, one of ordinary skill in the art will appreciate that each feature or element can be used alone or in any combination with the other features and elements. In addition, although process steps are described above in a particular order, the steps can be performed in other desirable orders.

The methods, processes, modules, and systems described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a ROM, a RAM, a register, cache memory, semiconductor memory devices, magnetic media such as internal hard disks and removable disks, magneto-optical media, and optical media such as CD-ROM disks, and DVDs. A processor in association with software may be used to implement a radio frequency transceiver for use in a WTRU, UE, terminal, base station, RNC, or any host computer.

Further embodiments herein may be formed by supplementing an embodiment with one or more element from any one or more other embodiment herein, and/or substituting one or more element from one embodiment with one or more element from one or more other embodiment herein.

It is understood, therefore, that the disclosed subject matter is not limited to the particular embodiments disclosed, but is intended to cover all modifications which are within the spirit and scope of the disclosure as defined by the appended claims, the above description, and/or shown in the attached drawings.

What is claimed is:

1. A system for detecting a heartbeat with optimal characteristics for an electrophysiological (EP) mapping system that improves cardiac mapping annotations, the system comprising:
   a memory;
   a sensor; and
   one or more processors communicatively coupled to the memory and the sensor, wherein the one or more processors are collectively configured to:
   receive, from the sensor, a first heartbeat at an identified cardiac spatial location including first attribute information corresponding to the first heartbeat;
   receive, from the sensor, a second heartbeat at the identified cardiac spatial location including a second attribute information corresponding to the second heartbeat;
   perform a comparison of the first attribute information with the second attribute information, wherein the comparison includes comparing one or more of heart beat noise, local activation time (LAT), late potential, fractionation or body surface activation during a heart beat; and
   determine a selected heartbeat from the first heartbeat and the second heartbeat based on the comparison, wherein the selected heartbeat is utilized in the cardiac mapping annotations.

2. The system of claim 1, wherein the one or more processors are further collectively configured to:
   output the selected heartbeat to the EP mapping system.

3. The system of claim 1, wherein the one or more processors are further collectively configured to:
   store, using the memory, at least one of the first heartbeat including the first attribute information and the second heartbeat including the second attribute information in a database.

4. The system of claim 3, wherein the one or more processors are collectively configured to:
receive a first manual input that indicates to accept one of the first heartbeat and the second heartbeat from a physician, and
receive a second manual input from the physician that indicates to delete the other one of the first heartbeat and the second heartbeat at the same spatial location up to a threshold tolerance.

5. The system of claim 1, wherein the comparison is performed using machine learning.

6. The system of claim 1, wherein the first attribute information or the second attribute information comprises at least one of:
an intracardiac electrogram signal received by an electrode of a catheter;
an electrocardiogram signal received from a mapping electrode;
an electrocardiogram signal received by one or more body surface electrodes;
a tissue proximity indication (TPI) of the mapping electrode at a time of a reference annotation;
a force value detected by a force sensor of a mapping catheter;
a spatial location of the mapping electrode at the reference annotation;
a respiration status vector around the reference annotation;
a position of the reference annotation inside a respiration cycle;
a difference between a current respiration cycle length and a previous respiration cycle length;
a ratio of the current respiration cycle length and the previous respiration cycle length;
a difference between the current respiration cycle length and an average or median respiration cycle length;
a ratio of the current respiration cycle length and the average or median respiration cycle length;
an indication of whether a physician manually accepted a respective heartbeat into the EP mapping system or deleted the heartbeat; or
a distance of the mapping electrode at a current reference annotation from the spatial location of the same electrode at a previous reference annotation.

7. The system of claim 1, wherein the comparison is a binary determination.

8. The system of claim 1, wherein at least one of the comparison or determining the selected heartbeat is performed using a neural network.

9. The system of claim 8, wherein the neural network is a convolutional neural network.

10. A method for detecting a heartbeat with optimal characteristics for an electrophysiological (EP) mapping system that improves cardiac mapping annotations, the method comprising:
receiving, from a sensor, first data comprising a first heartbeat at an identified cardiac spatial location including first attribute information corresponding to the first heartbeat;
receiving, from the sensor, second data comprising a second heartbeat at the identified cardiac spatial location including second attribute information corresponding to the second heartbeat;
performing a comparison of the first data with the second data, wherein the comparison includes comparing one or more of heart beat noise, local activation time (LAT), late potential, fractionation or body surface activation during a heart beat; and
outputting a selected heartbeat from among the first heartbeat and the second heartbeat based on the comparison, wherein the selected heartbeat is utilized in the cardiac mapping annotations.

11. The method of claim 10, further comprising outputting the selected heartbeat to the EP mapping system.

12. A system for detecting a mapping annotation for an electrophysiological (EP) mapping system that improves cardiac mapping annotations, the system comprising:
a memory;
a sensory; and
one or more processors communicatively coupled to the memory, wherein the one or more processors are collectively configured to:
receive, from the sensor, input data comprising attribute data for each of a plurality of heartbeats obtained at the same spatial location;
perform a comparison of the attribute data for each of the plurality of heartbeats with predefined threshold values wherein the comparison includes comparing one or more of heart beat noise, local activation time (LAT), late potential, fractionation or body surface activation during a heart beat; and
determine a selected heartbeat to use as the mapping annotation from among the plurality of heart beats based on the comparison wherein the selected heartbeat is utilized in the cardiac mapping annotations.

13. The system of claim 12, wherein the one or more processors are further collectively configured to:
output the selected heartbeat to the EP mapping system.

14. The system of claim 12, wherein one of the plurality of heartbeats is manually acquired by a physician in the EP mapping system.

15. The system of claim 12, wherein the comparison is performed using:
a machine learning algorithm.

16. The system of claim 12, wherein the attribute data comprises at least one of:
an intracardiac electrogram signal received by an electrode of a catheter;
an electrocardiogram signal received from a mapping electrode;
an electrocardiogram signal received by one or more body surface electrodes;
a local annotation time of an acquired heartbeat;
a tissue proximity indication (TPI) of the mapping electrode at the time of a reference annotation;
a force value detected by a force sensor of a mapping catheter a spatial location of the mapping electrode at the reference annotation;
a respiration gating status;
a respiration status vector around the reference annotation;
a position of the reference annotation inside a respiration cycle;
a difference between a current respiration cycle length and a previous respiration cycle length;
a ratio of the current respiration cycle length and the previous respiration cycle length;
a difference between the current respiration cycle length and an average or median respiration cycle length;
a ratio of the current respiration cycle length and the average or median respiration cycle length;

an indication of whether a physician manually accepted a heartbeat into the EP mapping system or deleted the heartbeat;

an indication of whether there was any body surface activation at a time of this heartbeat; or a distance of the mapping electrode at a current reference annotation from the spatial location of the same electrode at a previous reference annotation.

17. The system of claim 12, wherein at least one of the comparison or the determining the selected heartbeat is performed using a neural network.

18. The system of claim 17, wherein the neural network is a recurrent neural network (RNN).

19. The system of claim 18, wherein the heartbeat that is determined to be used as the mapping annotation as an input to train the RNN.

20. The system of claim 12, wherein the determination of the heartbeat to use as the mapping annotation is compared against a gold standard database to validate its accuracy.

21. A method for improving a mapping annotation for an electrophysiological (EP) mapping system by a machine learning algorithm, comprising:

receiving, from a sensor, input data comprising attribute data for each of a plurality of heartbeats obtained at the same spatial location;

performing a comparison of the attribute data for each of the plurality of heartbeats with predefined threshold values;

determining a selected heartbeat from among the plurality of heartbeats to use as the mapping annotation based on the comparison of heart beat noise, local activation time (LAT), late potential, fractionation, or body surface activation during a heart beat; and outputting the selected heart beat to the EP mapping system, wherein the selected heartbeat is utilized in the cardiac mapping annotations.

22. The method of claim 21, wherein one of the plurality of heartbeats is manually acquired by a physician in the EP mapping system; and the method further comprising training the machine learning algorithm to learn to determine which of the plurality of heartbeats to use as the mapping annotation based on results of the heartbeat acquired by the physician in the EP mapping system.

* * * * *

UNITED STATES PATENT AND TRADEMARK OFFICE
CERTIFICATE OF CORRECTION

PATENT NO. : 12,239,449 B2
APPLICATION NO. : 17/341917
DATED : March 4, 2025
INVENTOR(S) : Eliyahu Ravuna et al.

It is certified that error appears in the above-identified patent and that said Letters Patent is hereby corrected as shown below:

In the Specification

In Column 3, Line 47, delete "application" and insert -- application; --, therefor.
In Column 3, Line 62, delete "illustrated" and insert -- illustrates --, therefor.
In Column 4, Line 33, delete "can" and insert -- that can --, therefor.
In Column 6, Line 65, delete "a, smart phone" and insert -- a smartphone --, therefor.
In Column 8, Line 4, delete "read only system memory (ROM)" and insert -- read-only memory (ROM) --, therefor.
In Column 8, Lines 34-35, delete "integrated device electronics" and insert -- integrated drive electronics --, therefor.
In Column 15, Line 54, delete "pints" and insert -- points --, therefor.
In Column 17, Line 51, delete "connectionistic" and insert -- connectionist --, therefor.
In Column 18, Line 60, delete "of" and insert -- or --, therefor.
In Column 23, Line 60, delete "a" and insert -- by a --, therefor.
In Column 25, Line 25, delete "still" and insert -- skill --, therefor.
In Column 29, Line 50, delete "be" and insert -- to be --, therefor.
In Column 32, Line 31, delete "than" and insert -- then --, therefor.
In Column 34, Line 47, delete "in" and insert -- is --, therefor.
In Column 36, Line 64, delete "user name" and insert -- username --, therefor.
In Column 37, Line 54, delete "to that" and insert -- so that --, therefor.

In the Claims

In Column 38, Lines 51-52, in Claim 1, delete "heart beat" and insert -- heartbeat --, therefor.
In Column 38, Lines 53-54, in Claim 1, delete "heart beat;" and insert -- heartbeat; --, therefor.
In Column 40, Line 1, in Claim 10, delete "heart beat" and insert -- heartbeat --, therefor.
In Column 40, Line 3, in Claim 10, delete "heart beat;" and insert -- heartbeat; --, therefor.
In Column 40, Line 25, in Claim 12, delete "heart beat" and insert -- heartbeat --, therefor.
In Column 40, Line 27, in Claim 12, delete "heart beat;" and insert -- heartbeat; --, therefor.

Signed and Sealed this
Twenty-ninth Day of April, 2025

Coke Morgan Stewart
*Acting Director of the United States Patent and Trademark Office*

In Column 40, Line 29, in Claim 12, delete "heart beats" and insert -- heartbeats --, therefor.
In Column 40, Lines 39-40, in Claim 15, delete "performed using:
a machine learning algorithm." and insert -- performed using a machine learning algorithm. --, therefor.
In Column 41, Line 15, in Claim 19, delete "that is" and insert -- is --, therefor.
In Column 42, Line 9, in Claim 21, delete "heart beat" and insert -- heartbeat --, therefor.
In Column 42, Line 11, in Claim 21, delete "heart beat;" and insert -- heartbeat; --, therefor.
In Column 42, Line 12, in Claim 21, delete "heart beat" and insert -- heartbeat --, therefor.